(12) United States Patent
Ries et al.

(10) Patent No.: US 11,883,673 B2
(45) Date of Patent: Jan. 30, 2024

(54) ELECTRONICS ASSEMBLY FOR IMPLANTABLE MEDICAL DEVICE

(71) Applicant: Medtronic, Inc., Minneapolis, MN (US)

(72) Inventors: Andrew J. Ries, Lino Lakes, MN (US); Chunho Kim, Phoenix, AZ (US); Mark E. Henschel, Phoenix, AZ (US); Robert A. Munoz, Andover, MN (US); Christopher T. Kinsey, East Bethel, MN (US); Jeffrey S. Voss, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 338 days.

(21) Appl. No.: 17/071,463

(22) Filed: Oct. 15, 2020

(65) Prior Publication Data

US 2021/0121705 A1 Apr. 29, 2021

Related U.S. Application Data

(60) Provisional application No. 62/927,329, filed on Oct. 29, 2019.

(51) Int. Cl.
*A61N 1/375* (2006.01)

(52) U.S. Cl.
CPC ....... *A61N 1/3754* (2013.01); *A61N 1/37512* (2017.08)

(58) Field of Classification Search
CPC ............................ A61N 1/3754; A61N 1/37512
See application file for complete search history.

(56) References Cited

U.S. PATENT DOCUMENTS

| 8,433,409 | B2 * | 4/2013 | Johnson ................. A61N 1/378 607/9 |
| 2010/0305629 | A1 * | 12/2010 | Lund ................... H01M 50/469 607/2 |
| 2012/0172892 | A1 | 7/2012 | Grubac et al. |
| 2013/0230995 | A1 * | 9/2013 | Ivey ......................... F21K 9/90 29/874 |
| 2013/0325086 | A1 | 12/2013 | Sommer et al. |
| 2016/0296760 | A1 * | 10/2016 | Sahabi ................. A61N 1/0573 |
| 2017/0100597 | A1 * | 4/2017 | Barror ................ A61N 1/37223 |
| 2017/0127543 | A1 | 5/2017 | Day et al. |
| 2018/0333586 | A1 | 11/2018 | Wasson et al. |
| 2019/0083779 | A1 | 3/2019 | Yang et al. |

(Continued)

OTHER PUBLICATIONS

International Search Report and Written Opinion of International Application No. PCT/US2020/057587, dated Feb. 3, 2021, 12 pp.

*Primary Examiner* — Brian T Gedeon
(74) *Attorney, Agent, or Firm* — Shumaker & Sieffert, P.A.

(57) ABSTRACT

In some examples, an implantable medical device includes a battery, an electronics module electrically connected to the battery, and an elongated housing comprising a side wall positioned between the battery and an end cap, wherein the electronics module is positioned within the elongated housing between the battery and the end cap. The implantable medical device also includes an electrical contact assembly comprising a first spring contact and a second spring contact. The electrical contact assembly of the implantable medical device is positioned within the elongated housing between the electronics module and the battery or the end cap.

15 Claims, 16 Drawing Sheets

(56) References Cited

U.S. PATENT DOCUMENTS

| | | |
|---|---|---|
| 2019/0209845 A1 | 7/2019 | Stadler et al. |
| 2020/0001093 A1* | 1/2020 | Thom .................. A61N 1/3787 |
| 2020/0136301 A1* | 4/2020 | Durse ................ H01R 13/2442 |

* cited by examiner

ELECTRONICS ASSEMBLY FOR IMPLANTABLE MEDICAL DEVICE

This application claims the benefit of U.S. Provisional Patent Application 62/927,329, filed Oct. 29, 2019, the entire content of which is incorporated herein by reference.

TECHNICAL FIELD

The disclosure relates to medical devices, and more particularly to the structure and design of medical devices.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at the target site. The pulse generator may provide electrical stimulation to the target site and/or monitor cardiac electrical activity at the target site via the electrodes.

Other implantable pacemakers are configured to be implanted entirely within a chamber of the heart. Such pacemakers may be referred to as intracardiac pacing devices or leadless pacing devices, and may include one or more electrodes on their outer housings to deliver therapeutic electrical signals and/or sense intrinsic depolarizations of the heart. Such pacemakers may be positioned within or outside of the heart and, in some examples, may be anchored to a wall of the heart via a fixation mechanism.

SUMMARY

In general, this disclosure is directed to techniques for an implantable medical device including a battery, an electronics module, and an electrical contact assembly configured to hold and connect the electronics module in place. The electrical contact assembly includes at least two spring contacts for connecting to the electronics module. The battery, electronics module, and electrical contact assembly are arranged in an elongated housing that includes an enclosing side wall and an end cap. The arrangement of the components within the housing according to the techniques of this disclosure can result in a less complex and less expensive manufacturing process than other arrangements.

In one example, an implantable medical device includes a battery, an electronics module electrically connected to the battery, and an elongated housing comprising a side wall extending between the battery and an end cap. The electronics module is positioned within the elongated housing between the battery and the end cap. The implantable medical device also includes an electrical contact assembly comprising a first spring contact and a second spring contact. The electrical contact assembly is positioned within the elongated housing between the electronics module and the battery or is positioned within the elongated housing between the electronics module and the end cap.

Another example is an implantable medical device including a battery, a battery header, and a first feedthrough electrically connected to a first pole of the battery. The first feedthrough extends through the battery header. The implantable medical device also includes an elongated housing comprising a side wall extending between the battery header and an end cap. The implantable medical device further includes an electrical contact assembly mounted to the battery header and comprising a first spring contact and a second spring contact. The first spring contact is electrically connected to the first feedthrough. The implantable medical device includes an electronics module positioned within the housing between the battery header and the end cap. The electronics module is pressed against the first and second spring contacts of the electrical contact assembly, whereby the electronics module is electrically connected to the battery.

Other examples include an implantable medical device includes a battery, a battery header, and a feedthrough electrically connected to a cathode of the battery and extending through the battery header. The implantable medical device also includes an elongated tubular housing extending between a first end and a second end, wherein the first end is fixed to the battery header. The implantable medical device further includes an electronics header assembly comprising an end cap and an electronics module supported by the end cap. The implantable medical device includes an electrical contact assembly comprising a first spring contact and a second spring contact. The end cap of the electronics header assembly is fixed to the second end of the tubular housing. The electrical contact assembly is positioned within the tubular housing between the electronics module and the battery header. The first spring contact provides an electrical connection between the electronics module and battery cathode, and the elongated tubular housing provides an electrical connection between the electronics module and the battery anode.

Other examples include a method for assembling an implantable medical device. The method includes providing a battery module comprising a battery, a battery header, and a feedthrough electrically connected to a cathode of the battery and extending through the battery header. The method also includes mounting an electrical contact assembly to the battery header, the electrical contact assembly comprising a first spring contact and a second spring contact. The method further includes electrically connecting the first spring contact to the feedthrough. The method includes mounting an elongated tubular housing to the battery header about the electrical contact assembly, electrically connecting the elongated tubular housing to an anode of the battery, and inserting an electronics module into an open end of the tubular housing and translating the electronics module through the tubular housing into contact with the first and second spring contacts of the electrical contact assembly. The method also includes mounting an end cap to the open end of the tubular housing, whereby the electronics module is pushed against the first and second spring contacts, whereby the first and second spring contacts flex toward the battery header.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

In general, this disclosure describes example techniques related to the arrangement of an electronic module and one or more electrical contact assemblies in an implantable medical device. An electrical contact assembly includes spring contacts to hold the electronics module in place within the housing of the implantable medical device. The electronic module and the electrical contact assemblies may be positioned between a side wall and an end cap of the housing. The battery, which provides power to the electronics module, can be positioned on the other side of the side wall from the electronics module.

The arrangement described herein can allow for simpler and fastest manufacturing process for implantable medical devices. For example, the one or more electrical contact assemblies may eliminate the need for soldering or other more labor intensive techniques for establishing electrical connections during assembly. The arrangement may also save space, allowing for smaller implantable medical devices using the techniques of this disclosure.

Figure 1:
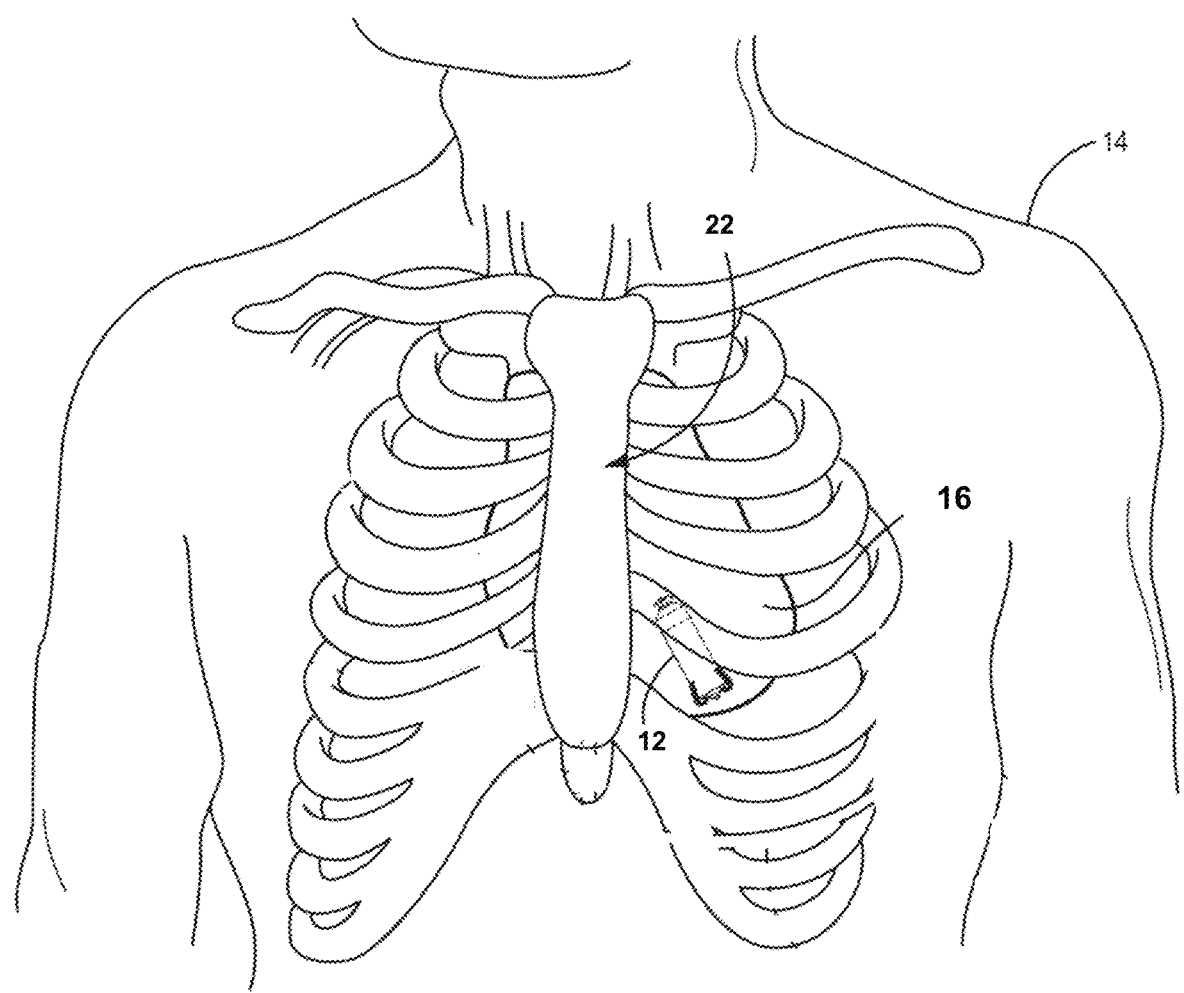
FIG. 1 is a conceptual diagram illustrating an example cardiac medical device system implanted within a patient.

FIG. 1 is a conceptual diagram illustrating an example pacing device 12 implanted within a patient 14. Pacing device 12 is an example of an implantable medical device that may include an arrangement of an electronics module and one or more electrical contact assemblies as described herein. Pacing device 12 may be, for example, an implantable leadless pacing device that is configured for implantation entirely within one of the chambers of heart 16, and that provides electrical signals to heart 16 beneath sternum 22 via electrodes carried on the housing of pacing device 12.

Pacing device 12 is generally described as being attached within a chamber of heart 16 as an intracardiac pacing device. In other examples that are consistent with aspects of this disclosure, pacing device 12 may be attached to an external surface of heart 16, such that pacing device 12 is disposed outside of heart 16 but can pace a desired chamber. In one example, pacing device 12 is attached to an external surface of heart 16, and one or more components of pacing device 12 may be in contact with the epicardium of heart 16. Pacing device 12 is schematically shown in FIG. 1 attached to a wall of a ventricle of heart 16 via one or more fixation elements (e.g. tines, helix, etc.) that penetrate the tissue. These fixation elements may secure pacing device 12 to the cardiac tissue and retain an electrode (e.g., a cathode or an anode) in contact with the cardiac tissue. Pacing device 12 may be implanted at or proximate to the apex of the heart. In other examples, a pacing device may be implanted at other ventricular locations, e.g., on the free-wall or septum, an atrial location, or any location on or within heart 16.

Figure 2:
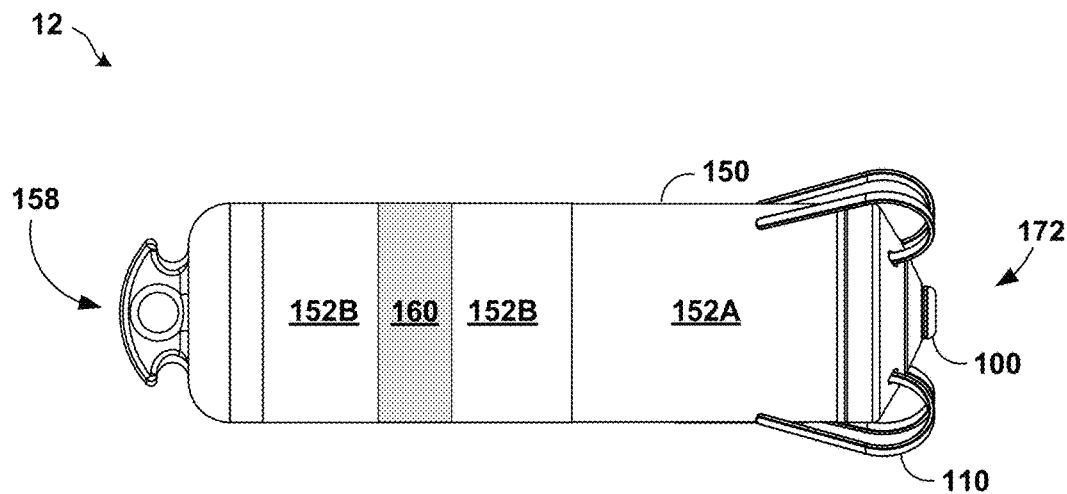
FIG. 2 is a conceptual illustration of an example configuration of a pacing device.

FIG. 2 is a conceptual illustration of an example configuration of pacing device 12. Pacing device 12 is configured to be implanted within a chamber of a heart of a patient, e.g., to monitor electrical activity of the heart and/or provide electrical therapy to the heart. In the example shown in FIG. 2, pacing device 12 includes outer housing 150, a plurality of fixation tines 110 and electrodes 100 and 160.

Outer housing 150 has a size and form factor that allows pacing device 12 to be entirely implanted within a chamber of a heart of a patient. In some examples, outer housing 150 may have a cylindrical (e.g., pill-shaped) form factor. Pacing device 12 may include a fixation mechanism configured to fix pacing device 12 to cardiac tissue. For example, in the example shown in FIG. 2, pacing device 12 includes fixation tines 110 extending from housing 150 and configured to engage with cardiac tissue to substantially fix a position of housing 150 within the chamber of the heart 16. Fixation tines 110 are configured to anchor housing 150 to the cardiac tissue such that pacing device 12 moves along with the cardiac tissue during cardiac contractions. Fixation tines 110 may be fabricated from any suitable material, such as a shape memory material (e.g., Nitinol). Although pacing device 12 includes a plurality of fixation tines 110 that are configured to anchor pacing device 12 to cardiac tissue in a chamber of a heart, in other examples, pacing device 12 may be fixed to cardiac tissue using other types of fixation mechanisms, such as, but not limited to, barbs, coils, and the like.

Housing 150, also referred to as an elongated housing, houses electronic components of pacing device 12, e.g., sensing circuitry for sensing cardiac electrical activity via electrodes 100 and 160 and therapy generation circuitry for delivering electrical stimulation therapy via electrodes 100 and 160. Electronic components may include any discrete and/or integrated electronic circuit components that implement analog and/or digital circuits capable of producing the functions attributed to pacing device 12 described herein. In some examples, housing 150 may also house components for sensing other physiological parameters, such as acceleration, pressure, sound, and/or impedance. Although shown with both electrodes 100 and 160, in some examples, housing 150 may only include one or the other of electrodes 100 and 160.

Additionally, housing 150 may also house a memory that includes instructions that, when executed by processing circuitry housed within housing 150, cause pacing device 12 to perform various functions attributed to pacing device 12 herein. In some examples, housing 150 may house communication circuitry that enables pacing device 12 to communicate with other electronic devices, such as a medical device programmer. In some examples, housing 150 may house an antenna for wireless communication. Housing 150 may also house a power source, such as a battery. Housing 150 can be hermetically or near-hermetically sealed in order to help prevent fluid ingress into housing 150.

Pacing device 12 is configured to sense electrical activity of the heart and deliver electrical stimulation to the heart via electrodes 100 and 160. Electrode 100 and/or electrode 160 may be mechanically connected to housing 150. As another example, electrode 100 and/or electrode 160 may be defined by an outer portion of housing 150 that is electrically conductive. For example, electrode 160 may be defined by a conductive portion of housing 150.

In the example of FIG. 2, housing 150 includes a first portion 152A and a second portion 152B. Portion 152B may, in some examples, define at least part of a power source case that houses a power source (e.g., a battery) of pacing device 12. The power source case may house a power source (e.g., a battery) of pacing device 12. In some examples, the portion 152B may include the conductive portion of housing that forms electrode 160.

Electrodes 100 and 160 are electrically isolated from each other. Electrode 100 may be referred to as a tip electrode, and fixation tines 110 may be configured to anchor pacing device 12 to cardiac tissue such that electrode 100 maintains contact with the cardiac tissue. In some examples, a portion of housing 150 may be covered by, or formed from, an insulative material to isolate electrodes 100 and 160 from each other and/or to provide a desired size and shape for one or both of electrodes 100 and 160. Electrode 160 may be a portion of housing 150, e.g., housing portion 152B, that does not include such insulative material. Electrode 160 can be most or all of housing 150, but most of housing 150 (other than electrode 160, may be covered with an insulative coating. Additionally or alternatively, electrode 160 may be coated with materials to promote conduction. In some examples, electrode 160 may be part of a separate ring portion of housing 150 that is conductive. Electrodes 100 and 160, which may include conductive portion(s) of housing 16, may be electrically connected to at least some electronics of pacing device 12 (e.g., sensing circuitry, electrical stimulation circuitry, or both). In some examples, housing 150 may include an end cap 172, which may include a feedthrough assembly to electrically couple electrode 100 to the electronics within housing 150, while electrically isolating electrode 100 from housing 150, e.g., including electrode 160 or other conductive portions of housing 150.

In the example of FIG. 2, the proximal end of pacing device 12 includes a flange 158 that defines an opening. Flange 158 may enable medical instruments to attach to pacing device 12, e.g., for delivery and/or extraction of pacing device 12. For example, a tether that extends through a catheter inserted into heart 16 (FIG. 1) may be attached to flange 158 and/or threaded through the opening to implant or extract pacing device 12.

Figure 3:
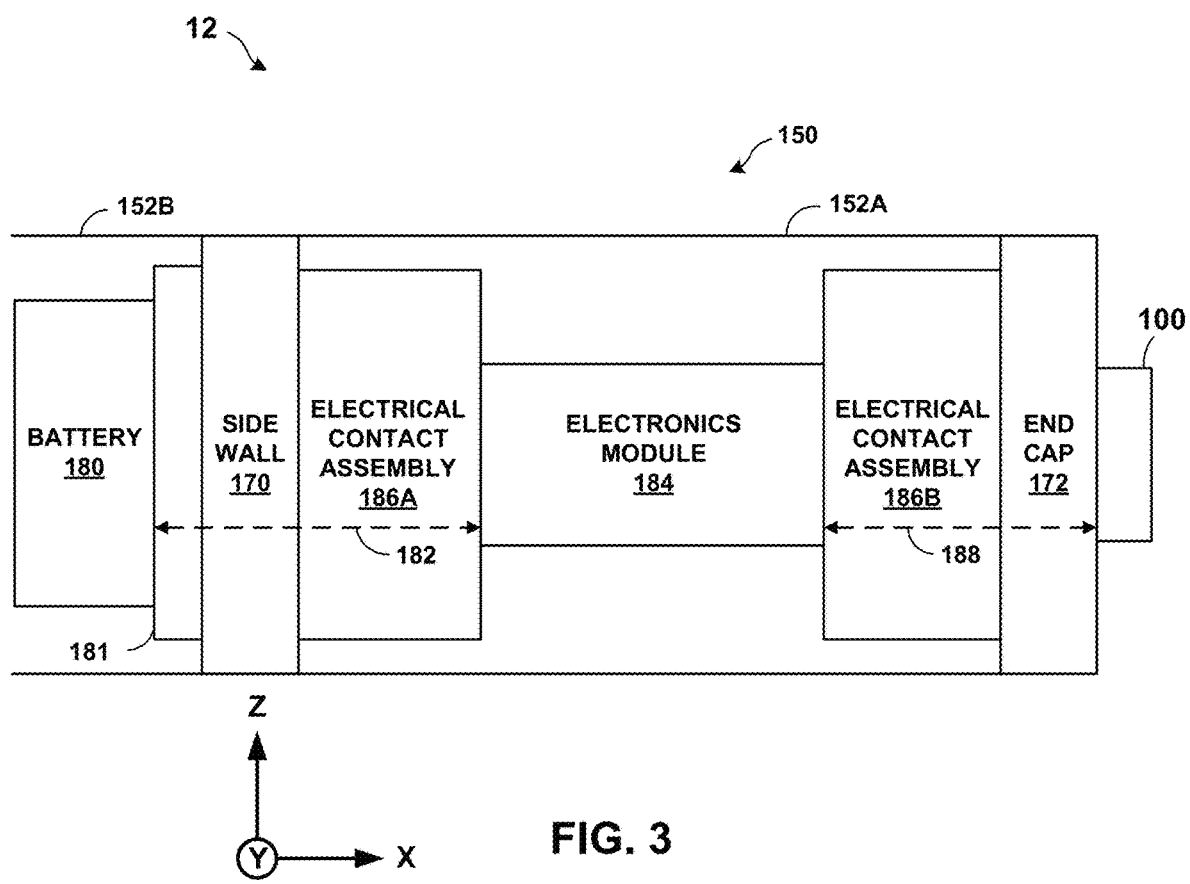
FIG. 3 is a block diagram of an implantable medical device including a battery, an electronics module, and an electrical contact assembly.

FIG. 3 is a block diagram of an example configuration of implantable medical device 12 including a battery 180, an electronics module 184, and an electrical contact assemblies 186A and 186B. Although the implantable medical device of FIG. 3 is described as pacing device 12, the structures shown in FIG. 3 can also be used in other implantable or external medical devices, such as cardioverter-defibrillators, physiological monitors, or neurostimulators, or any other electronic devices.

Housing 150 includes portions 152A and 152B and side wall 170 positioned within housing 150 between battery 180 and end cap 172. Side wall 170 can be positioned within housing portions 152B or 152A or at the boundary of housing portions 152A and 152B. In some examples, housing portions 152A and 152B are common with a pole of battery 180, such as the ground terminal (e.g., anode) of battery 180. In some examples, one or both of housing portions 152A and 152B is non-conductive. For example, housing portion 152A may be formed of a non-conductive material, such as sapphire, which may allow easier passage of electromagnetic signals from outside of housing 150 to antennae or the like within housing 150 then a metal or other conductive material.

As shown in the example of FIG. 3, side wall 170 extends across housing 150 between battery 180 on one side and electrical contact assemblies 186A and 186B and electronics module 184 on the other side. Side wall 170 may include at least one feedthrough to allow for electrical connection 182 between battery 180 and electronics module 184. As discussed above, end cap 172 may also include at least one feedthrough to allow for electrical connection 188 between electrode 100 and electronics module 184. Electronics module 184 is positioned between and pressed against electrical contact assemblies 186A and 186B. Electrical contact assembly 186B may be fixed to end cap 172 to provide mechanical support for electronics module 184. Additionally or alternatively, electric contact assembly 186A may be fixed to side wall 170 to provide mechanical support for electronics module 184.

Pacing device 12 may also include battery header 181 positioned between battery 180 and electric contact assembly 186A. Side wall 170 can form part of battery header 181, or side wall 170 can be positioned between battery header 181 and end cap 172, such as between battery header 181 and electric contact assembly 186A. Battery header 181, side wall 170, and electric contact assembly 186A may include means for electrically connecting battery to electronics module 184. For example, battery header 181, side wall 170, and/or electric contact assembly 186A may include feedthroughs and/or openings for creating an electrical connection between battery 180 and electronics module 184.

Electrical contact assemblies 186A and 186B may be positioned on either side of electronics module 184. Each of electrical contact assemblies 186A and 186B includes a spring contact for holding electronics module 184 in place and for providing electrical connections. Electronics module 184 can include a printed wiring board or a hybrid board with electronic components (integrated circuits, packages, capacitors, resistors, etc.) mounted on the board. In some examples, pacing device 12 includes only one of electrical contact assemblies 186A and 186B on one side of electronics module 184.

The design of pacing device 12 shown in FIG. 3 resolves many of the manufacturing issues with other implantable medical devices. For example, the manufacturing process for another implantable medical device may include laser soldering of battery and electrode feedthrough pins to create connections from the electronics module to the battery and electrode. The laser soldering may be difficult and expensive as compared to using electrical contact assemblies 186A and 186B to provide the electrical contacts between electronics module 184 and the battery and electrodes, which is possible in the design of pacing device 12. Electrical contact assemblies can reduce the cost and complexity of interconnect components, especially as compared to laser soldering.

Pacing device 12 can be manufactured with a single tube for housing portion 152A or as two tube sections for portion 152A. Using a single tube for housing portion 152A, in contrast to two sections, e.g., two half-pipes, lowers the cost and complexity of the encasement for pacing device 12. A single tube opens up new encasement options and can be manufactured from alternate materials. For example, a single sapphire tube for housing portion 152A can allow for wireless charging of battery 180 even when pacing device 12 is implanted within a patient. Additionally, using a single tube for housing 150 or using two single-tube portions 152A and 152B, as well as the layout of the components within housing 150 shown in FIG. 3, can reduce the overall size of pacing device 12, which is especially important for a device designed for implantation in the heart or pulmonary artery. A single tube reduces the manufacturing time for pacing device 12 because using two half-pipe sections means additional steps in the manufacturing process.

Use of a single tube may by enabled due the component interconnection methods described herein, which may remove the need for access to the components to complete the assembly and interconnect processes. Many interconnection methods, such as solder, conductive epoxy, and welding, require access to the joints between the components of pacing device 12. A split-case, half-pipe design allows closure of the encasement after the interconnection operation. On the other hand, spring contacts may allow a single tubular housing because the contact can be blind mated without access for a joining process between the spring contacts and the electronics module. The electric contact assemblies described herein can remove the need for gaining access to the assembly to complete the interconnection process. Thus, pacing device 12 may include a single tube because the manufacturing process may not include welding the electronics module to an electric contact assembly.

As shown in FIGS. 4-10 and 18A, electrical contact assemblies 186A and 186B can include spring contacts with spring fingers to make contact with electronics module 184. Electronics module 184 can be suspended between and/or held in place by the fingers of electrical contact assembly 186A and electrical contact assembly 186B. In examples in which electronics module 184 includes a circuit board or a wiring board, the spring fingers of electrical contact assemblies 186A and 186B can contact and electrically connect to the electrically conductive areas (e.g., the plated edges) of the board. The spring fingers can apply pressure to the pads on the board, e.g., the board edge, to hold electronics module 184 in place.

Figure 18A:
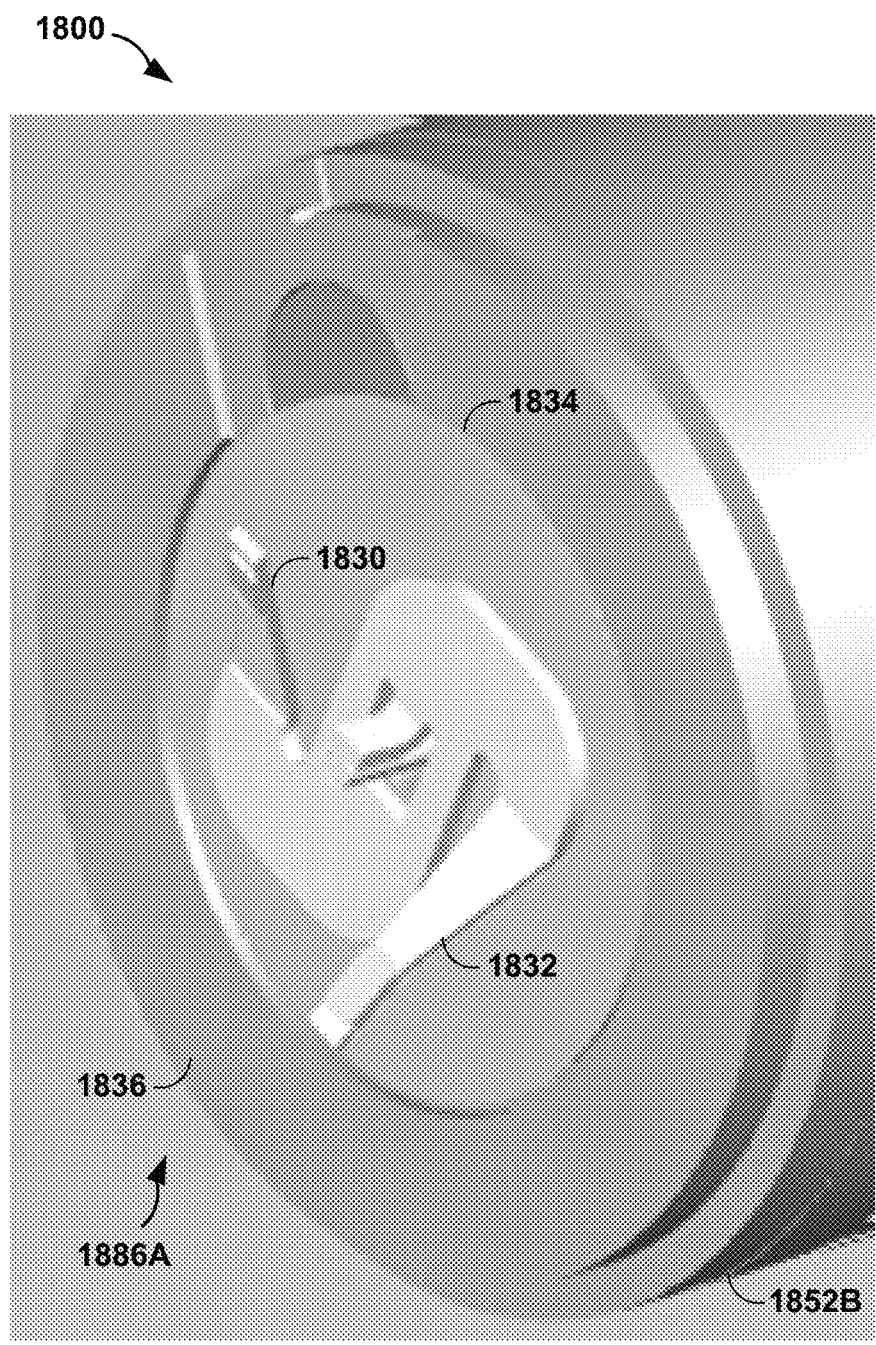
FIG. 18A is a diagram of an example implantable medical device including an electric contact assembly with two spring fingers, in accordance with one or more aspects of this disclosure.

FIGS. 4-10 show example designs for each of electrical contact assemblies 186A and 186B that includes four fingers. Four fingers provide redundant springs for mechanical and structural integrity for pacing device 12. In the four-finger implementation, each of electrical contact assemblies 186A and 186B can include two fingers of each polarity (e.g., the anode and cathode of battery 180). One or more of the poles of battery 180 are connected to the spring arms of electric contact assemblies 186A and/or 186B. In addition, FIG. 18A shows an example two-finger design for each of electrical contact assemblies 186A and 186B. The two fingers provide redundant springs for mechanical and structural integrity for pacing device 12.

The manufacturing and assembly process for pacing device 12 can include first forming housing portion 152B and side wall 170. The manufacturing process then includes the installation of battery 180 in housing portion 152B behind side wall 170 and sealing of side wall 170 to housing portion 152 to enclose battery 180 therein. Electrical contact assembly 186A is connected to side wall 170, and electrical connection 182 is formed between battery and electrical contact assembly 186A. Electrical connections 182 and 188 may be hermetic feedthrough conductive paths that pass the otherwise hermetic housing of pacing device 12. In examples in which housing 150 includes two single-tube pieces (e.g., portions 152A and 152B in a split-case design), portion 152A can be installed over electrical contact assembly 186A and attached to side wall 170 and portion 152B.

Electronics module 184 is then inserted into the open end of portion 152A put into contact with electrical contact assembly 186A. End cap 172 is mounted on portion 152A, where end cap 172 may have electrical contact assembly 186B already attached. Electrical contact assembly 186B comes into contact with electronics module 184 as end cap 172 is mounted on portion 152A. Mounting end cap 172 pushes electrical contact assembly 186B against electronics module 184, which pushes electronics module 184 against electrical contact assembly 186A. End cap 172 may include a feedthrough extending through end cap 172 to create an electrical connection with an electrode (e.g., electrode 100) on end cap 172. Thus, the board of electronics module 184 is loaded onto the pins of electrical contact assemblies 186A and 186B, providing electrical connection between the electrical contacts and the electronic circuitry of electronics module 184.

In some examples, there may be three electrical paths that leave the hermetic chamber. On the end with battery 180, pacing device 12 may include a battery pin (e.g., electrical connection 182) and case ground, where the battery pin can be connected to a first pole (e.g., cathode) of battery 180, and the case ground can be connected to a second pole (e.g., anode) of battery 180. Case ground on the end with battery 180 can be connected to housing portion 152B. On the end with end cap 172, pacing device 12 may include an electrode pin (e.g., electrical connection 188 and electrode 100) and case ground. Case ground on the end with end cap 172 can be connected to housing portion 152A. The case ground on each end may be electrical connected across pacing device 12 (e.g., only one case ground for the entire device), or there may be two separate case ground elements where there is an insulating material between the elements. For example, a sapphire or ceramic tube around electronics module 184 can result in two case ground potentials. Even in examples in which there is a single case ground, the case ground may be redundantly connected to electric contact assemblies 184A and 184B. In some examples, there may be more than one pin on each end, resulting in more than three electrical paths passing through the hermetic seal.

Electric contact assembly 186A may have a single-channel configuration or a multiple-channel configuration. In a single-channel configuration, electric contact assembly 186A provides a single electrical channel between battery 180 and electronics module 184. In the single-channel configuration, the spring contact(s) of electric contact assembly 186A can be electrically connected to a first pole of battery 180, and housing portions 152A and 152B can be electrically connected to a second pole of battery 180.

In a double-channel configuration, electric contact assembly 186A provides two electrical channels between battery 180 and electronics module 184. In the double-channel configuration, a first set of one or more spring contacts of electric contact assembly 186A can be electrically connected to a first pole of battery 180, and a second set of one or more spring contacts of electric contact assembly 186A can be electrically connected to a second pole of battery 180. In the double-channel configuration, housing portions 152A and 152B can also be electrically connected to one of the poles of battery 180. A single-channel configuration allows for a simpler construction and simpler assembly, as compared to a multiple-channel configuration, because of fewer electrical connections that are formed through electric contact assembly 186A.

Figure 4:
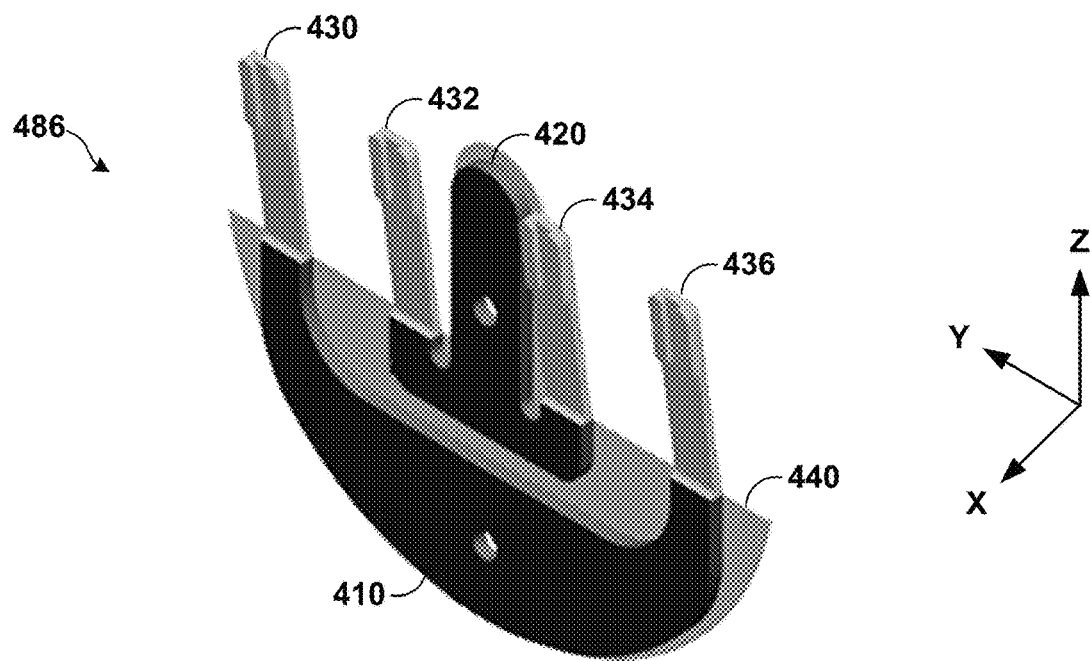
FIGS. 4-6 are diagrams of example electric contact assemblies, in accordance with one or more aspects of this disclosure.
Figure 5:
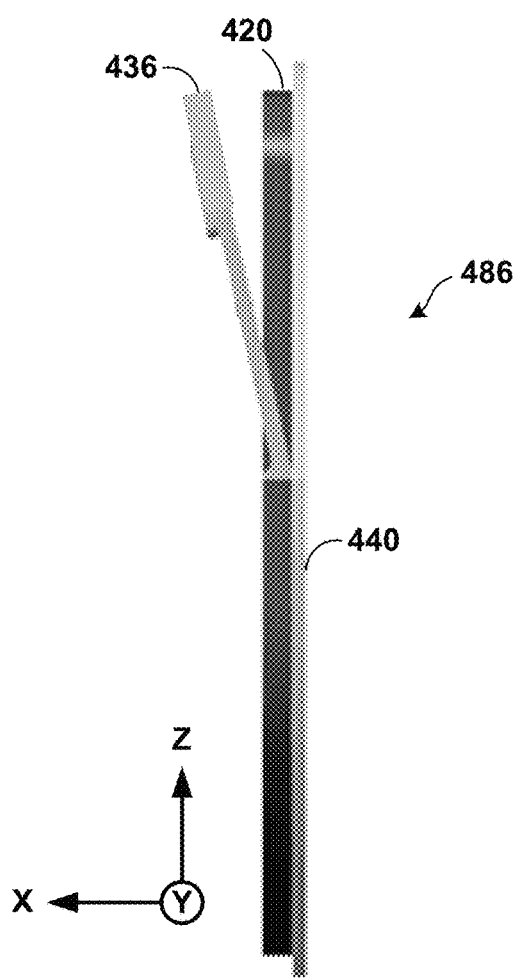
Figure 6:
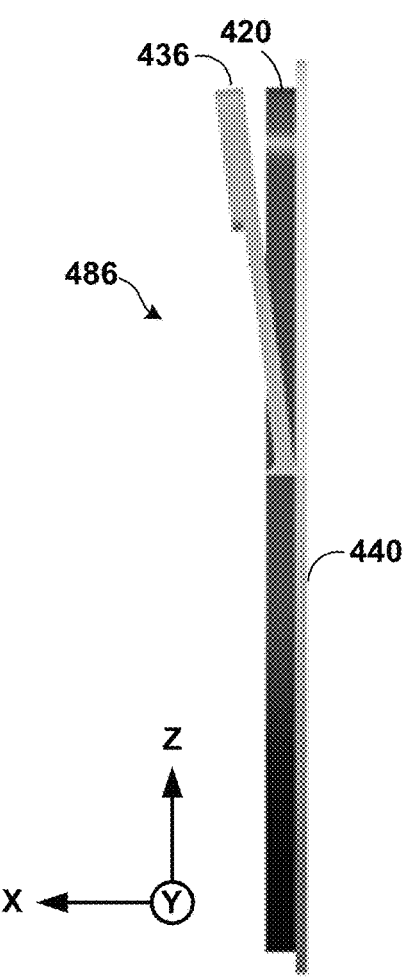

FIGS. 4-6 are diagrams of example electric contact assembly 486, in accordance with one or more aspects of this disclosure. Electric contact assembly 486 includes conductive portions 410 and 420, spring contacts 430, 432, 434, and 436, and insulative portion 440. Electric contact assembly 486 is just one example configuration of electric contact assemblies 186A and 186B shown in FIG. 3. In some examples, electric contact assembly 486 may include more than or fewer than four spring contacts. For example, electric contact assembly 486 may include only one spring contact. In addition, although FIG. 3 depicts pacing device 12 as including two electric contact assemblies, an implantable medical device may include any number of electric contact assemblies, including only one electric contact assembly.

In the example shown in FIGS. 4-6, conductive portion 410 is electrically connected to spring contacts 430 and 436, and conductive portion 420 is electrically connected to spring contacts 432 and 434. Thus, electric contact assembly 486 may be used in a double-channel configuration, where each of conductive portions 410 and 420 is electrically connected to a respective pole of a battery, and conductive portion 410 is electrically isolated from conductive portion 420. For example, conductive portion 410, along with spring contacts 430 and 436, may be electrically connected to a first pole (e.g., an anode) of the battery. Conductive portion 420, along with spring contacts 432 and 434, may be electrically connected to a second pole (e.g., a cathode) of the battery. In a single-channel configuration, conductive portion 410 may be electrically connected to conductive portion 420, such that all of spring contacts 430, 432, 434, and 436 are all connected to the same pole of a battery.

After assembly of an implantable medical device, an electronics module (not shown in FIGS. 4-6) may be in contact with spring contacts 430, 432, 434, and 436. For example, the plated edges of a circuit board of an electronics module may be in contact with spring contacts 430, 432, 434, and 436, forming one or more electrical connections between spring contacts 430, 432, 434, and 436 and the components on the circuit board. Additionally or alternatively, the metalized ends of an electronics module may be in contact with spring contacts 430, 432, 434, and 436. Thus, each of spring contacts 430, 432, 434, and 436 can act as a power rail or power supply for the electronics module, such as a high-side power rail (e.g., Vcc or Vdd) and/or a low-side power rail (e.g., reference ground).

In a multiple-channel configuration, outside spring contacts 430 and 436 may be electrically connected to a case ground, and inside spring contacts 432 and 434 may be electrically connected to a feedthrough pin. The center hole of conductive portion 410 can be welded or soldered to a conductor that is connected to case ground, or to case ground itself, and the center hole of conductive portion 420 can be welded or soldered to a feedthrough pin. In some examples, electric contact assembly 486 may include more than two electrical paths such that there may be a connection to case ground, and two or more connections to two or more pins. Thus, electric contact assembly 486 may include additional spring contacts for connecting to another pin.

Electric contact assembly 486 may also include one or more holes or openings in conductive portions 410 and 420 and insulative portion 440. These openings may receive feedthroughs pins for making electrical connections to a battery through a housing of the battery, which may be positioned in the negative x-axis relative to electric contact assembly 486. A conductive element, such as wire, pin, or a metal plate, can be fed through the holes in conductive portions 410 and 420 and insulative portion 440 or form the electrical connections between each of conductive portions 410 and 420 and the battery. In some examples, the feedthrough includes a conductive pin extending through an electrically insulating material, such as glass, of the side wall.

Conductive portions 410 and 420 and insulative portion 440 may be arranged coplanar in the y-axis and z-axis directions. Electric contact assembly 486 is shown with a circular shape for installation inside a cylindrical-shaped implantable medical device, where the x-axis is the longitudinal axis of the implantable medical device. Spring contacts 430, 432, 434, and 436 extending in the x-axis direction out of the plane of conductive portions 410 and 420 and out of the plane of insulative portion 440. FIGS. 5 and 6 show a side view of electric contact assembly 486 with spring contact 436 in two positions. In FIG. 5, spring contact 436 is extending in the x-axis direction to a greater extent than shown in FIG. 6, where spring contact 436 is shown closer to the plane of conductive portions 410 and 420 and insulative portion 440. As shown in FIGS. 4-6, spring contacts 430, 432, 434, and 436 may be pushed back towards insulative portion 440 when in contact with an electronics module.

Insulative portion 440 is an insulative backing for conductive portions 410 and 420. Conductive portions 410 and 420 are mounted to insulative portion 440 in the example shown in FIGS. 4-6. Spring contacts 430, 432, 434, and 436 are shown in FIGS. 4-6 as biased away from insulative portion 440. However, when an electronics module is pressed against spring contacts 430, 432, 434, and 436, spring contacts 430, 432, 434, and 436 may be configured to flex or bend back towards insulative portion 440.

Spring contacts 430, 432, 434, and 436 may also be referred to as "spring arms," "contact arms," or "spring fingers" because spring contacts 430, 432, 434, and 436 can hold an electronics module in place. Spring contacts 430, 432, 434, and 436 are shown in FIGS. 4-6 as straight (e.g., without bends), except for the joint between each of spring contacts 430, 432, 434, and 436 and the respective one of conductive portions 410 and 420. For example, spring contact 430 has a straight, rectangular shape with a flexed joint where spring contact meets conductive portion 410. In some examples, an electric contact assembly includes two spring contacts, where each spring contact is electrically connected to a pole of the battery. As compared to an electric contact assembly with only one or two spring contacts, four spring contacts 430, 432, 434, and 436 of electric contact assembly 486 provide redundancy and additional structural integrity to reduce the likelihood of single-point failures. However, an electric contact assembly with one or two spring contacts may still provide structural integrity while reducing the number of mechanical and/or electrical connections that are formed between the electric contact assembly and an electronics module.

FIG. 5 is an example of the position of spring contact 436 in an unstressed state, and FIG. 6 is an example of position of spring contact 436 in a stressed state, when an electronics module is being held by spring contacts 430, 432, 434, and 436. Spring contacts 430, 432, 434, and 436 may be flexible, allowing spring contacts 430, 432, 434, and 436 to be pressed into the position shown in FIG. 6. When spring contact 436 is pressed into the position shown in FIG. 6 by an electronics module, the positive z-axis end of spring contact 436 may exert a force on the electronics module in the positive x-axis direction. This force can hold or suspend the electronics module in place without any welding or laser soldering of the electronics module to an electric contact assembly. The springiness and flexibility of spring contacts 430, 432, 434, and 436 is based on the length and material used for spring contacts 430, 432, 434, and 436.

Figure 7:
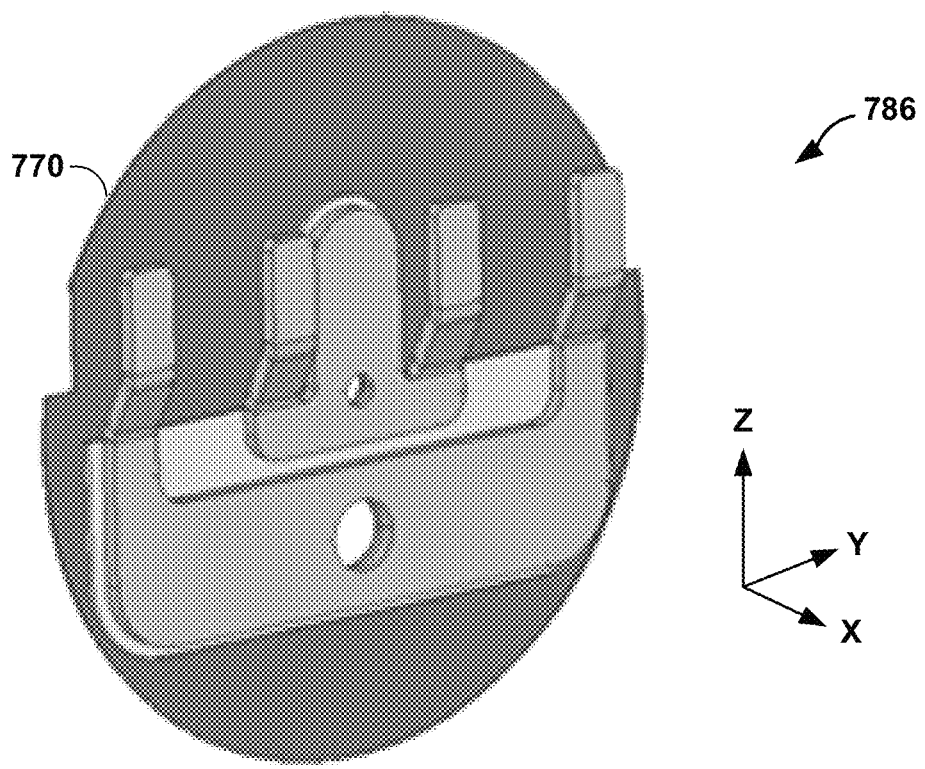
FIGS. 7 and 8 are diagrams of an example electric contact assembly attached to an insulative backing, in accordance with one or more aspects of this disclosure.
Figure 8:
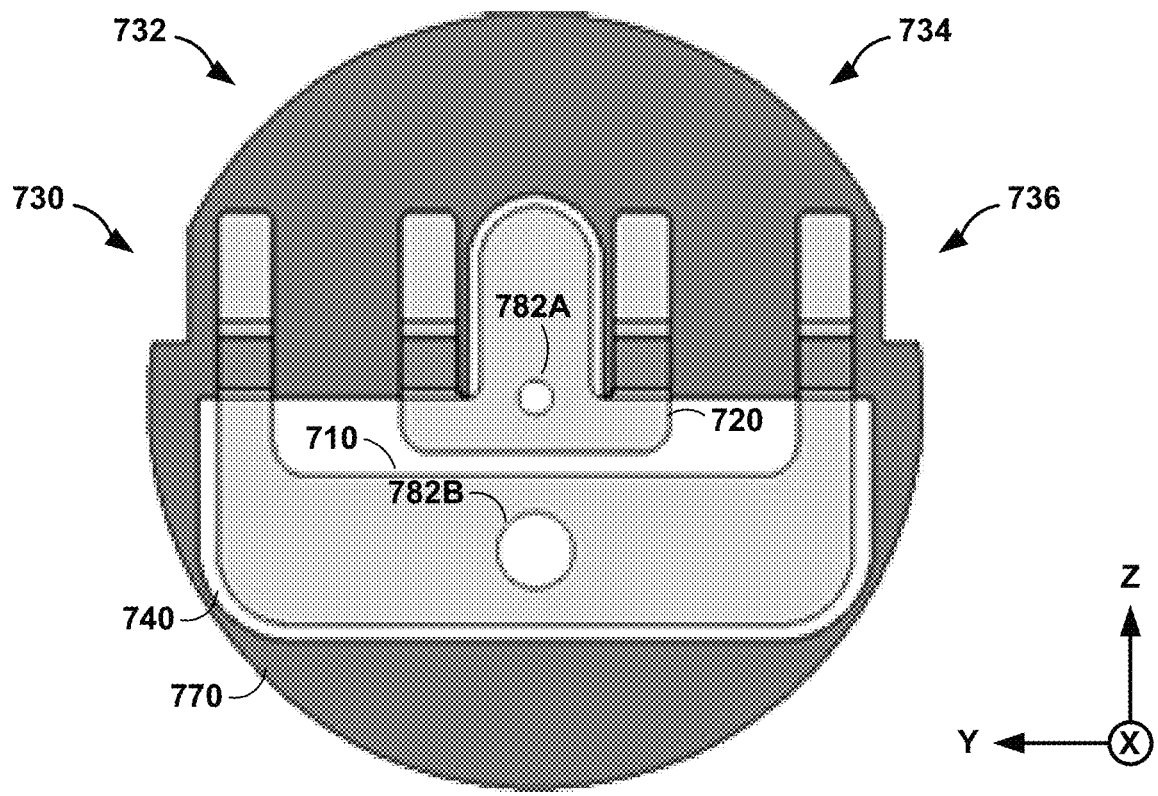

FIGS. 7 and 8 are diagrams of an example electric contact assembly 786 attached to an insulative backing 770, in accordance with one or more aspects of this disclosure. Electric contact assembly 786 includes conductive portions 710 and 720, spring contacts 730, 732, 734, and 736, and insulative portion 740. In a multiple-channel configuration, each of conductive portions 710 and 720 is electrically connected to a respective pole of a battery, conductive portion 710 is electrically isolated from conductive portion 720. In a single-channel configuration, conductive portion 710 may be electrically connected to conductive portion 720.

Electric contact assembly 786 is just one example configuration of electric contact assemblies 186A and 186B shown in FIG. 3. In some examples, electric contact assembly 786 may include more than or fewer than four spring contacts. In addition, although FIG. 3 depicts pacing device 12 as including two electric contact assemblies, an implantable medical device may include any number of electric contact assemblies, including only one electric contact assembly.

Electric contact assembly 786 may be formed by welding portions 710, 720, 740, and/or 770 using contact welding. Electric contact assembly 786 includes openings 782A and 782B for creating an electrical connection between conductive portions 710 and 720 and a battery. The electrical connection can be formed by a feedthrough that extends through insulative backing 770, a side wall, and/or a battery header. The battery header may be connected to insulative backing 770 opposite spring contacts 730, 732, 734, and 736.

Conductive portions 710 and 720 may include titanium with an example thickness of approximately 0.002 to 0.005 inches. Insulative portion 740 can be polyimide bonded to conductive portions 710 and 720. Spring contacts 730, 732, 734, and 736 may include an electrically conductive plating with a material such as gold, silver, titanium, or another metal. Insulative backing 770 can include a loose insulator material.

Figure 9A:
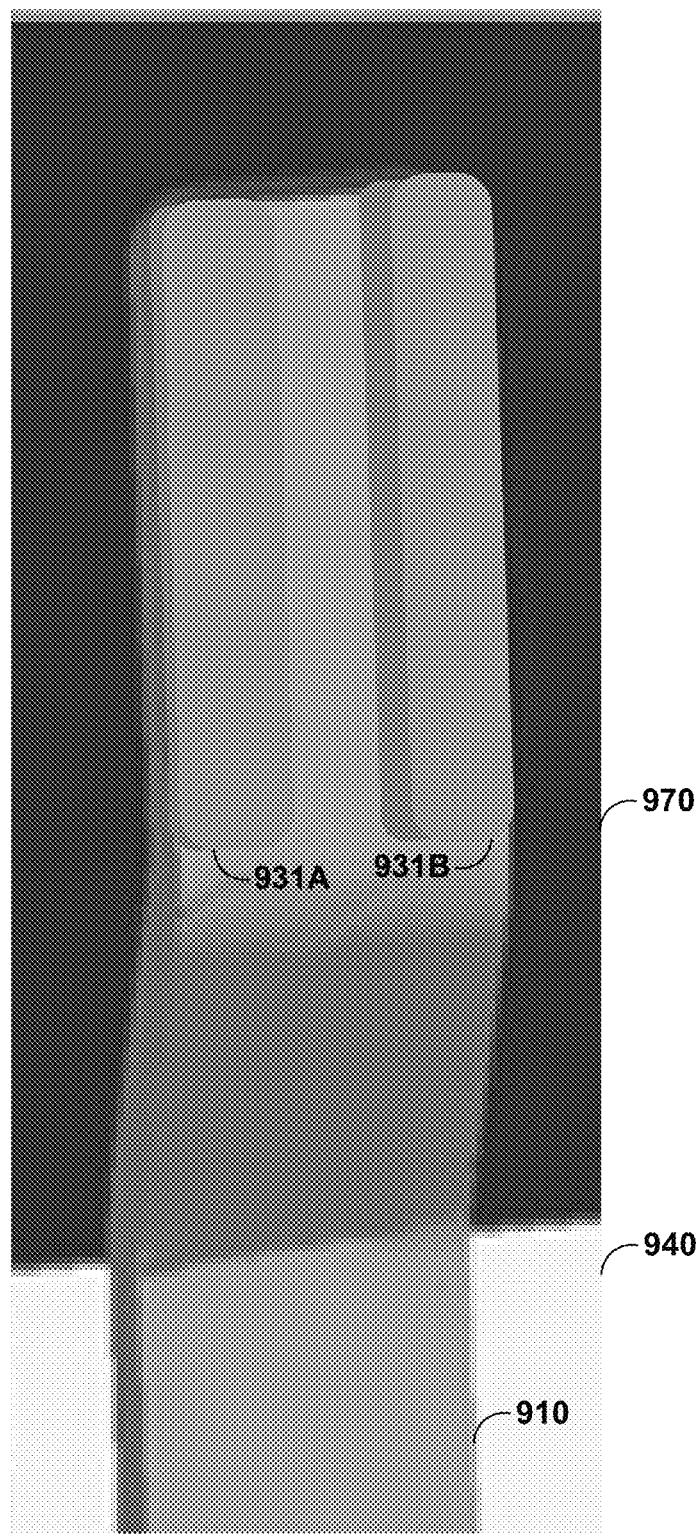
FIGS. 9A and 9B are diagrams of an example spring contact of an electric contact assembly, in accordance with one or more aspects of this disclosure.
Figure 9B:
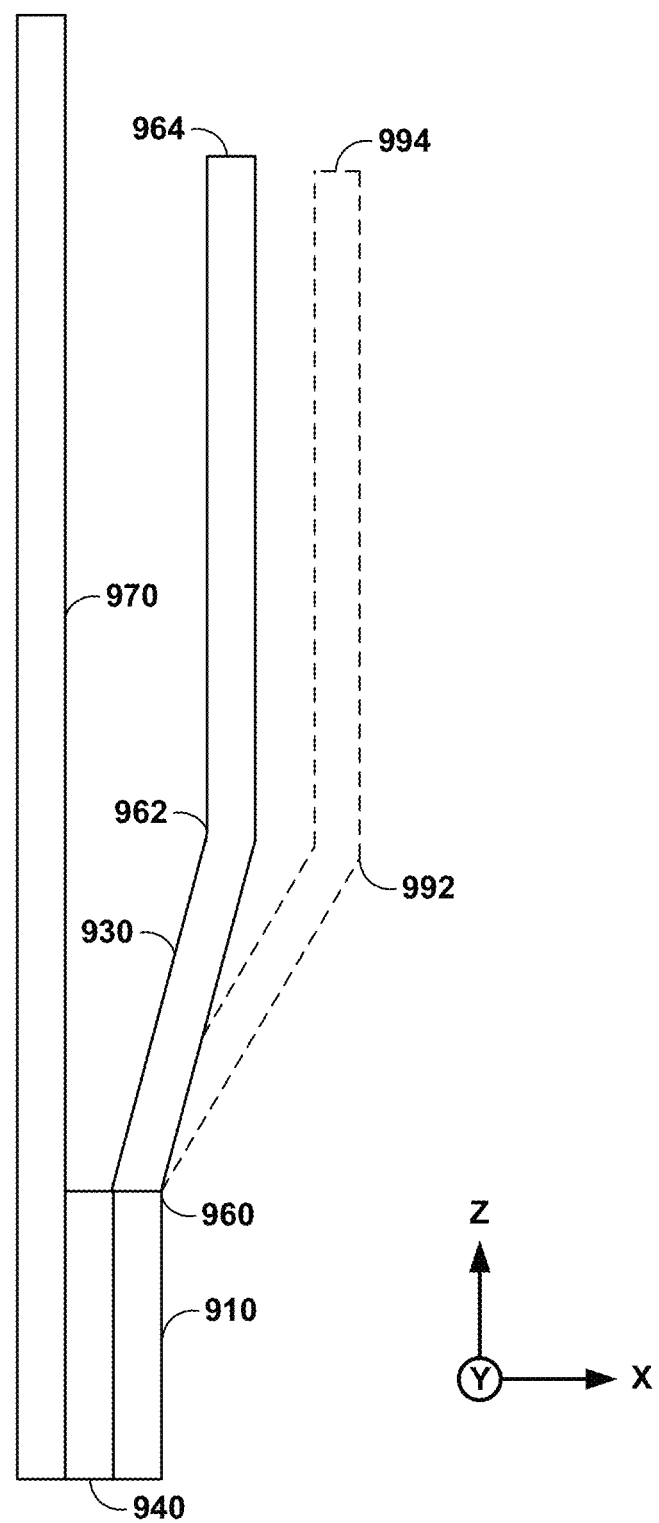

FIGS. 9A-9B are diagrams of an example spring contact 930 of an electric contact assembly, in accordance with one or more aspects of this disclosure. In the example shown in FIG. 9A, spring contact 930 includes two ribs 931A and 931B (e.g., raised contact surfaces) that protrude from spring contact 930 for making contact with an electronics module. Ribs 931A and 931B shown in FIG. 9A are raised islands on spring contact finger 930 for contact interface with the plated edge of a circuit board. Ribs 931A and 931B may be plated with a metal such as gold, silver, aluminum, or another metal. Spring contact 930 may also have gold coverage on portions of spring contact 930 other than ribs 931A and 931B. Spring contact 930 may be titanium material or another suitable material that is 0.005 inches thick. Ribs 931A and 931B can increase the number of contact points between the electric contact assembly and a circuit board or wiring board.

The portion of spring contact 930 that does not have ribs 931A and 931B may be depth etched so that the titanium is only 0.002 to 0.003 inches to reduce the beam stiffness and created the raised profile of ribs 931A and 931B. The depth etching can result in a thicker metal at the pin weld for process margin and a thinner area in the beam to control forces. In some examples, ribs 931A and 931B can be formed using a process other than depth etching.

Ribs 931A and 931B may also hold the electronics module suspended in place. Spring contacts 430, 432, 434, and 436 illustrated in FIGS. 4-6, spring contacts 730, 732, 734, and 736 of FIGS. 7 and 8, or any spring contacts described herein may also include ribs with a structure similar to ribs 931A and 931B shown in FIG. 9A. In some examples, each spring contact can include one, two, three, or any other number of ribs for making contact with an electronics module.

Spring contact 930 shown in FIG. 9B has a different shape than spring contacts 430, 432, 434, and 436 shown in FIGS. 4-6. Spring contact 930 includes bend 960 where spring contact 930 meets conductive portion 910. Spring contact 930 also includes a bend 962 between joint 960 and end 964 of spring contact 930. Between bend 962 and end 964, spring contact 930 may extend parallel with the z-axis direction (e.g., coplanar with conductive portion 910, insulative portion 940, and side wall 970). Spring contact 930 is biased away from side wall 970, the battery, and the battery header so that spring contact 930 can flex towards side wall 970 when a circuit board is pressed against spring contact 930.

FIG. 9B shows spring contact 930 in two possible positions: an unconstrained position and an installed position. Bend 992 and end 994 show the unconstrained position when spring contact 930 is not in contact with an electric contact assembly. Bend 962 and end 964 show the installed position when an electric contact assembly is pushed against spring contact 930. The force applied by the electric contact assembly moves spring contact 930 in the negative x-axis direction.

Figure 10:
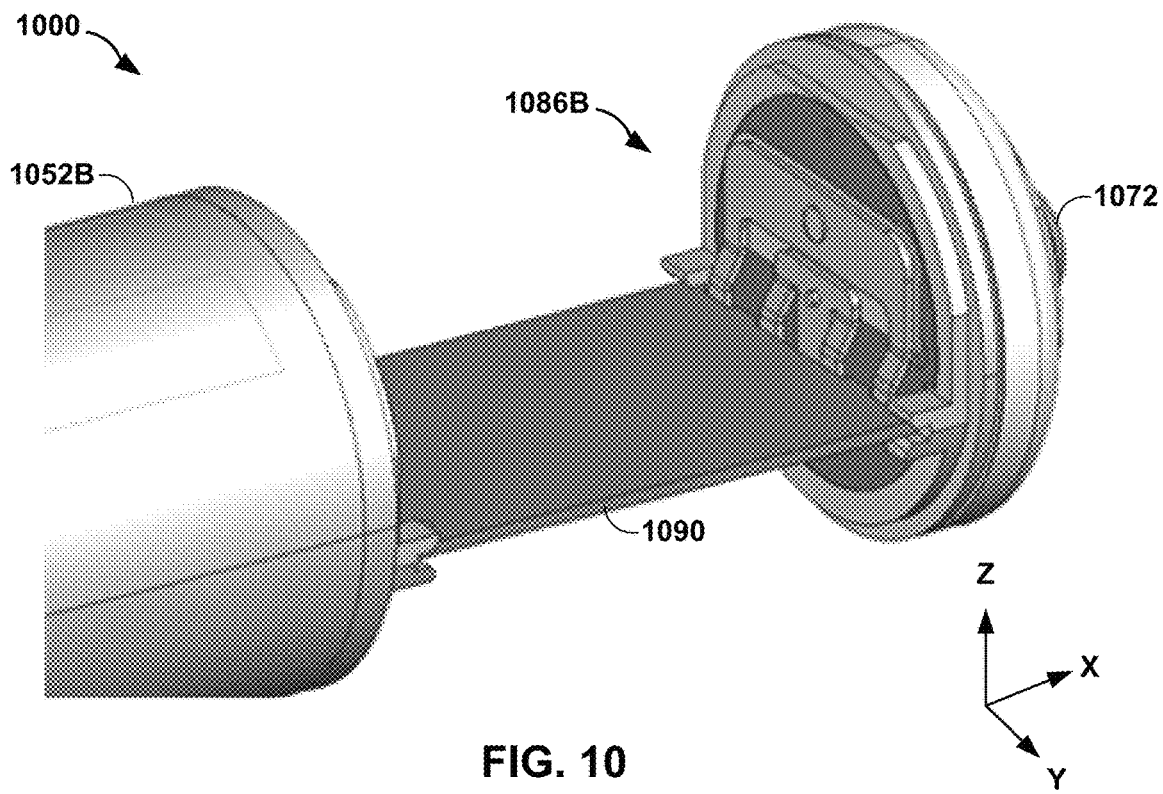
FIGS. 10 and 11 are diagrams of an example implantable medical device including the circuit board of an electronics module, in accordance with one or more aspects of this disclosure.
Figure 11:
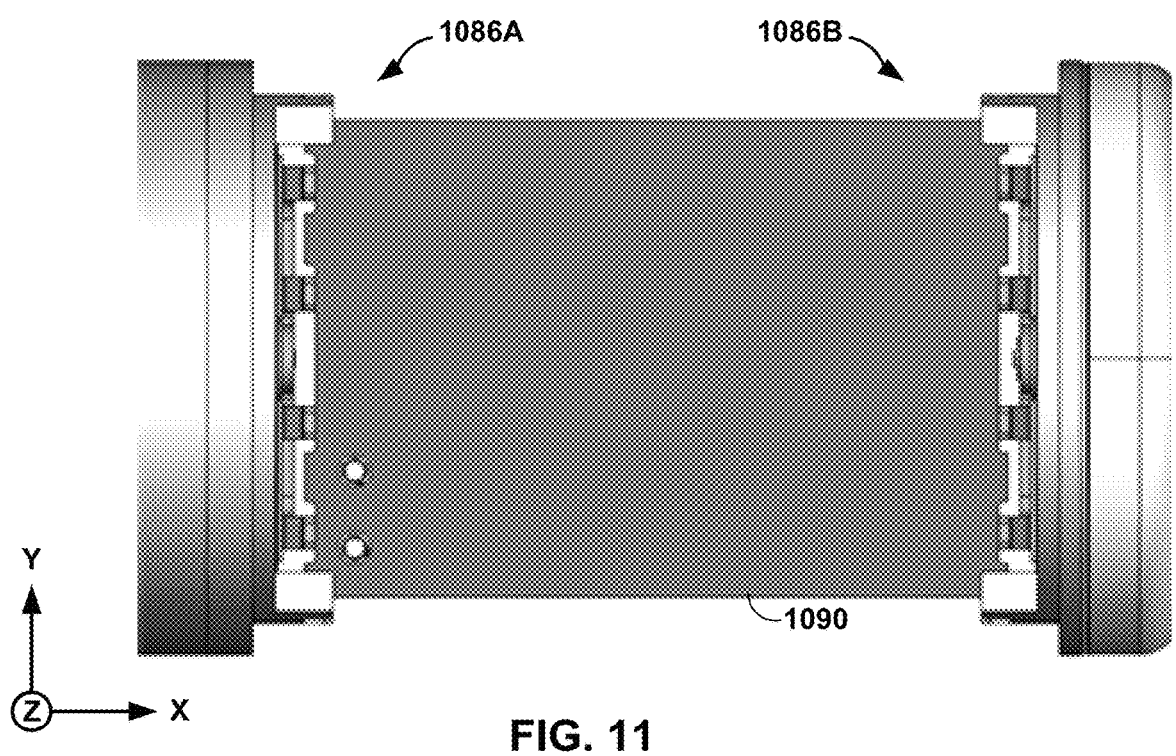

FIGS. 10 and 11 are diagrams of an example implantable medical device (e.g., implantable medical device 12) including the circuit board 1090 of an electronics module (e.g., electronics module 184), in accordance with one or more aspects of this disclosure. In the example shown in FIGS. 10 and 11, circuit board 1090 is suspended between electric contact assemblies 1086A and 1086B. Implantable medical device 100 is an example of a "dual spring on a circuit board" device, where the spring contacts of electric contact assemblies 1086A and 1086B may be pressed against circuit board 1090. Electric contact assembly 1086B is positioned proximate end cap 1072, and electric contact assembly 1086A is positioned proximate housing portion 1052B. A battery may be positioned within housing portion 1052B.

One or more of the spring contacts of electric contact assemblies 1086A and 1086B are in contact with the conductive portions of circuit board 1090. The spring contacts of electric contact assembly 1086A flex or bend towards the side wall and/or battery header when circuit board 1090 is held between electric contact assemblies 1086A and 1086B. The spring contacts of electric contact assemblies 1086A and 1086B may apply pressure on circuit board 1090 in the x-axis direction. For example, the plated spring contacts may be in contact with the plated edges of circuit board 1090. Spring contacts may form electrical connections between a battery (not shown in FIGS. 10 and 11) and the traces, vias, and mounted components of circuit board 1090. Circuit board 1090 may include a printed circuit board (PCB), a printed wiring board (PWB), a hybrid PCB/PWB, and/or any other type of board.

The spring contact(s) of electric contact assemblies 1086A and 1086B may be soldered or otherwise permanently attached to electronics module 1084. In some examples, the spring contact(s) of only one of electric contact assemblies 1086A and 1086B is permanently attached (e.g., soldered or glued) to electronics module 1084, while the spring contact(s) of the other of electric contact assemblies 1086A and 1086B is attached to electronics module 1084 in a non-permanent manner (e.g., pressed against).

Although each of electric contact assemblies 1086A and 1086B are depicted in FIGS. 10 and 11 with four spring contacts, electric contact assembly 1086A or 1086B may have only one spring contact. Additionally or alternatively, electric contact assembly 1086A or 1086B may have an electrical contact that does not include a spring. In examples in which electric contact assembly 1086A or 1086B has only one spring contact, the other electric contact assembly (e.g., the feedthrough end of electronics module 1084) may be soldered or otherwise permanently attached to electronics module 1084. The non-permanently attached side of electronics module 1084 may be pressed against the electric contact assembly, which may only have one spring contact. The one spring contact may be connected to, for example, the reference ground for implantable medical device 1000.

In some examples, an electronics module may include an electrically insulative housing mounted to circuit board 1090. The insulative housing may include end walls that come into contact with electric contact assemblies 1086A and 1086B. The end walls of the insulative housing may contain conductive pads and traces that contact and connect to the spring fingers of electric contact assemblies 1086A and 1086B. A first end wall may face the battery header and a second end wall may face end cap 1072. Each end wall may include a metalized area for contacting a spring contact and forming an electrical connection with the spring contact.

Figure 12:
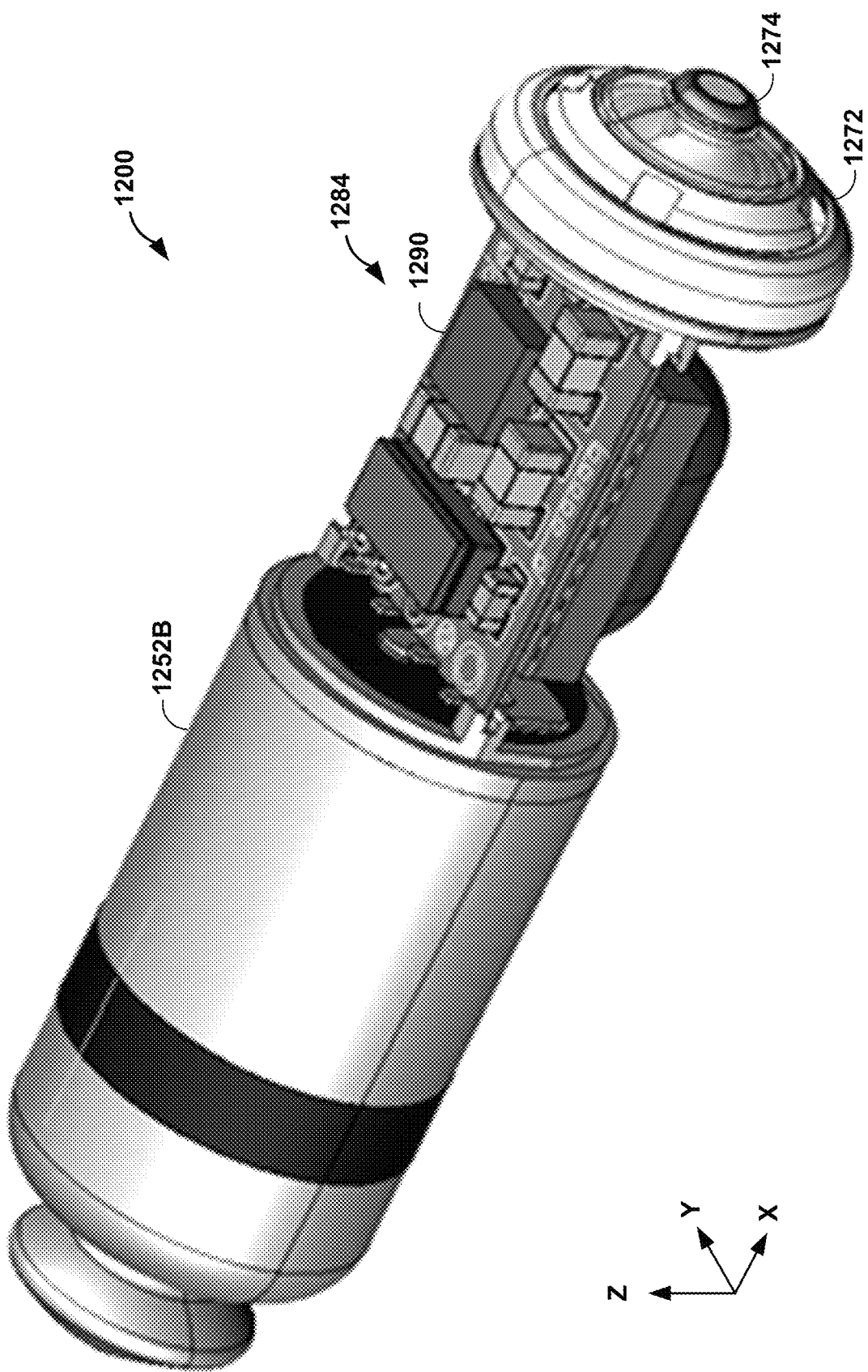
FIG. 12 is a diagram of an example implantable medical device including an electronics module with electronics components mounted on a circuit board, in accordance with one or more aspects of this disclosure.

FIG. 12 is a diagram of an example implantable medical device 1200 including an electronics module 1284 with electronics components mounted on a circuit board 1290, in accordance with one or more aspects of this disclosure. The components that are mounted on or attached to circuit board 1290 can include integrated circuits, capacitors, resistors, and/or any other electrical components. Electronics module 1284 may also include an antenna, either as an integrated circuit mounted on circuit board 1290 or as a patch antenna that is built into circuit board 1290. Implantable medical device 1200 includes a longitudinal axis along the x-axis. The major surface of circuit board 1290 faces the positive and negative z-axis directions, which are perpendicular to the x-axis direction.

Figure 13:
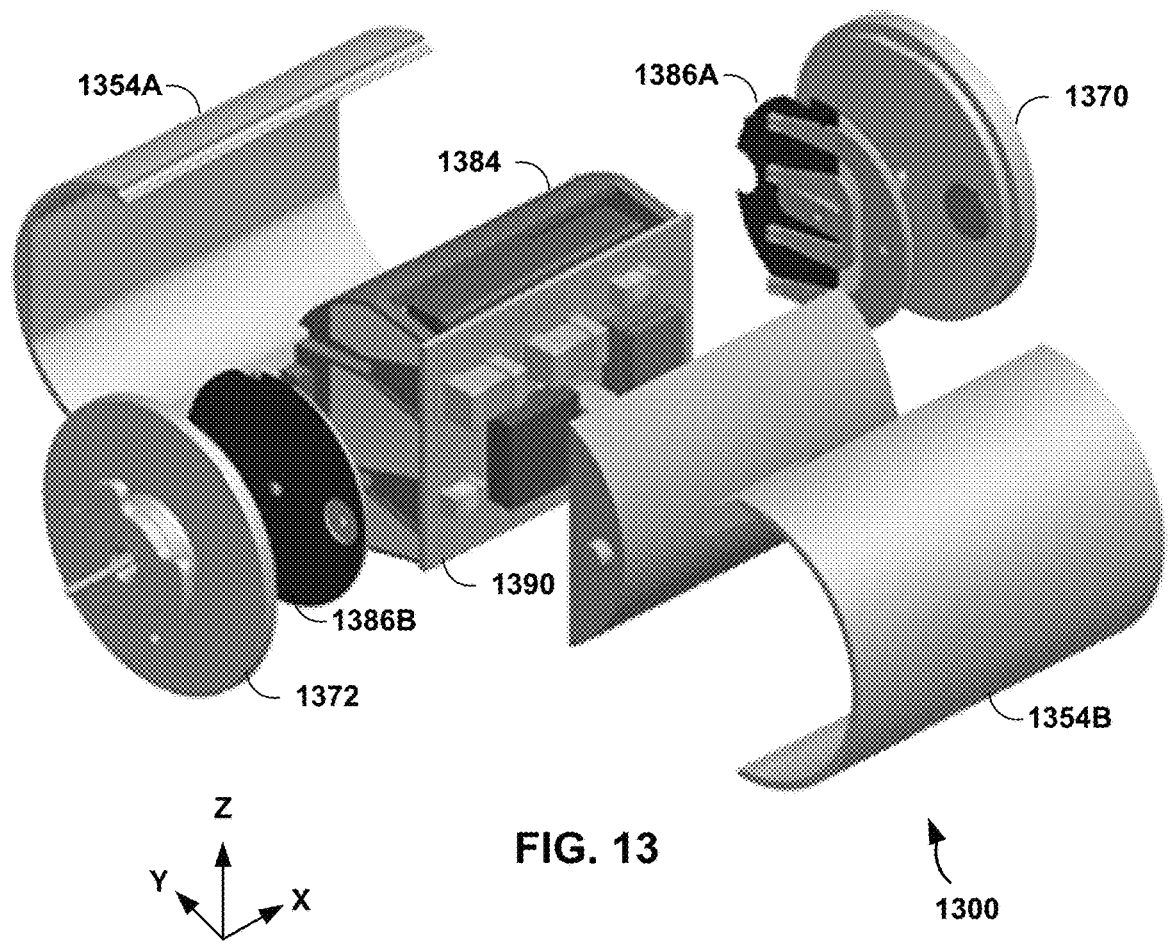
FIGS. 13 and 14 are exploded view diagrams of two example implantable medical devices, in accordance with one or more aspects of this disclosure.
Figure 14:
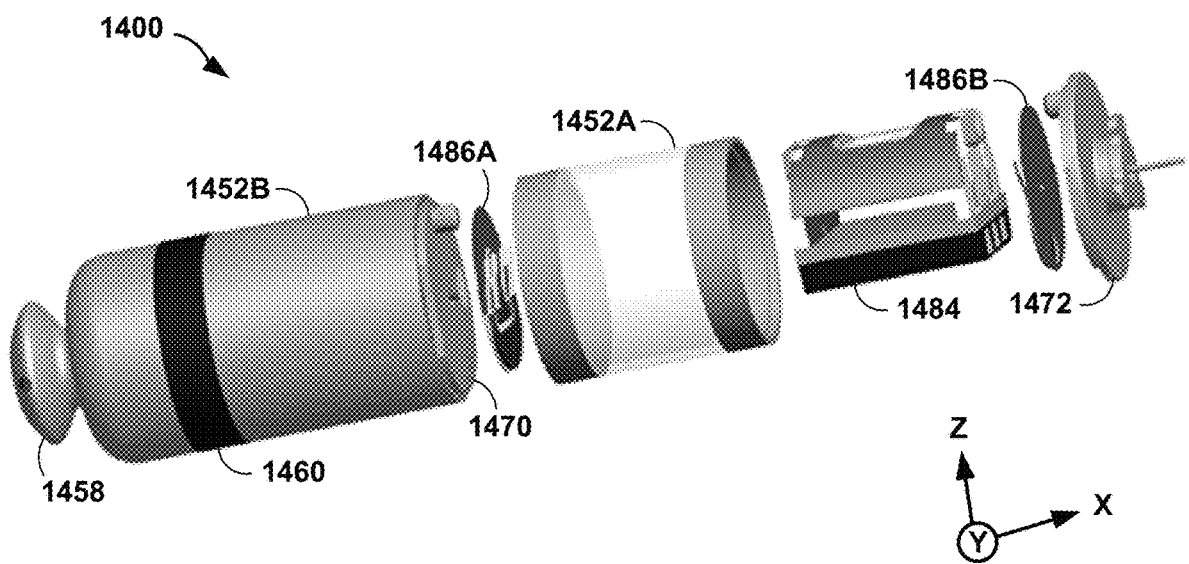

Implantable medical device 1200 is shown in FIG. 12 as including housing portion 1252B but without a second housing portion to reveal electronics module 1284. FIGS. 13 and 14 show two example configurations for the second housing portion. The second housing portion can have a cylindrical shape and extend from housing portion 1252B to end cap 1272. Electrode 1274 can be welded to the feedthrough conductive path that passes through the hermetic enclosure of implantable medical device 1200 to connect to a spring contact of an electric contact assembly.

FIGS. 13 and 14 are exploded view diagrams of two example implantable medical devices 1300 and 1400, in accordance with one or more aspects of this disclosure. Implantable medical device 1300 includes two half cylindrical housing portions 1354A and 1354B enclosing electronics module 1384. Implantable medical device 1300 also includes electric contact assemblies 1386A and 1386B to hold electronics module 1384 in place. The spring contacts of electric contact assemblies 1386A and 1386B can press against contact areas on electronics module 1384. Electronics module 1384 may include two contact areas on each side, where each contact area is configured to electrically connect to a pole of the battery on a first end of electronics module 1384. For example, electronics module 1384 may be electrically connected to the electrode feedthrough on the other end. The contact area on each side of electronics module 1384 may be a joint pad soldered to the circuit board of electronics module 1384. Electric contact assembly 1386A may be attached to side wall 1370, which can include a feedthrough for electrically connecting electronics module 1384 to a battery. Electric contact assembly 1386B may be attached to end cap 1372, which can include a feedthrough for electrically connecting electronics module 1384 to an electrode, such as electrode 100 (see FIGS. 2 and 3).

After electronics module 1384 is positioned on electric contact assembly 1386A, housing portions 1354A and 1354B can be installed to enclose electronics module 1384. During the manufacturing process, housing portions 1354A and 1354B can be put together to form a sleeve. Housing portion 1354A may be attached to housing portion 1354B by welding, laser soldering, or another attachment method. In some examples, a first one of housing portions 1354A and 1354B may be attached to side wall 1370 and/or end cap 1372 prior to positioning electronic module 1384, and then the second one of housing portions 1354A and 1354B (e.g., the "lid") may be attached to the side wall and the first housing portion to surround the electronic module. Electric contact assembly 1386B and end cap 1372 may be pressed against electronics module 1384 so that the spring contacts of electric contact assemblies 1386A and 1386B hold electronics module 1384 in place.

As shown in FIG. 13, electronics module 1384 includes a metalized housing that extends off circuit board 1390 of electronics module 1384 in the y-axis direction. Electronics module 1384 includes plastic housing with metalized doors, strips, or panels on the end of the plastic housing. Each spring contact of electric contact assemblies 1386A and 1386B may come in contact with a metalized door of electronics module 1384 to form an electrical connection. The metalized panels of electronics module 1384 can be soldered to circuit boar 1390.

Implantable medical device 1300 can be assembled by connecting housing portions 1354A and 1354B and welding housing portions 1354A and 1354B to end cap 1372. Electric contact assembly 1386B may have been already attached to end cap 1372 before housing portions 1354A and 1354B are welded to end cap 1372. Then electronics module 1384 can be slid into the space that is partially enclosed by housing portions 1354A and 1354B and end cap 1372. Side wall 1370, which is attached to the header of the battery, is added to the assembly to close the canister and trap electronics module 1384 between the spring contacts of electric contact assemblies 1386A and 1386B. Side wall 1370 can be welded to housing portions 1354A and 1354B.

FIG. 14 depicts implantable medical device 1400 includes two cylindrical housing portions 1452A and 1452B enclosing electronics module 1484. Implantable medical device 1400 also includes electric contact assemblies 1486A and 1486B to hold electronics module 1484 in place. Electric contact assembly 1486A may be attached to side wall 1470, which can include a feedthrough for electrically connecting electronics module 1484 to a battery. Side wall 1470 is attached to housing portion 1452B in the example shown in FIG. 14. Electric contact assembly 1486B may be attached to end cap 1472, which can include a feedthrough for electrically connecting electronics module 1484 to an electrode, such as metal fixation tines.

After housing portion 1452A can be installed, electronics module 1484 can be inserted into housing portion 1452A and positioned on electric contact assembly 1486A. Housing portion 1452A may include sapphire material that is covered by another material and/or is covered by another case. Additionally or alternatively, housing portion 1452A may include a titanium tube. Electric contact assembly 1486B and end cap 1472 may be pressed against electronics module 1484 so that the spring contacts of electric contact assemblies 1486A and 1486B hold electronics module 1484 in place. Housing portion 1452A may be attached to housing portion 1452B and end cap 1472 by welding, laser soldering, or another attachment method.

By using electric contact assemblies 1486A and 1486B, the assembly process may not include welding, soldering, or otherwise processing electronics module 1484 to electric contact assemblies 1486A and 1486B. The electrical connection between electronics module 1484 and electric contact assemblies 1486A and 1486B can be created using the assembly pressure of electronics module 1484 on the electric contact assemblies 1486A and 1486B. A single tube can be used for housing portion 1452A because electronics module 1484 can be inserted into housing portion 1452A and electrical connections can be formed between electronics module 1484 and the battery without welding. Therefore, electric contact assemblies 1486A and 1486B eliminate the need for welding, laser soldering, or other more labor-intensive techniques for establishing electrical connections during assembly. Moreover, electric contact assembly 1486A and 1486B take up less space, use simpler components, and eliminates the need for access to the components to complete the assembly and interconnect processes, as compared to other connection techniques. Thus, electric contact assemblies 1486A and 1486B may result in lower complexity and lower manufacturing costs, as compared to using two half-pipe sections for housing portion 1452A.

The single tube for housing portion 1452A may include materials such as sapphire, ceramics, other non-metallic materials, other electrically insulative materials, metallic materials, electrically conductive materials, and/or other materials. For example, housing portion 1452A may include titanium ends and a sapphire midsection. The use of titanium or other metals allows for welding. The titanium can be diffusion bonded to the sapphire at high temperatures, or the titanium may be gold-brazed.

Figure 15:
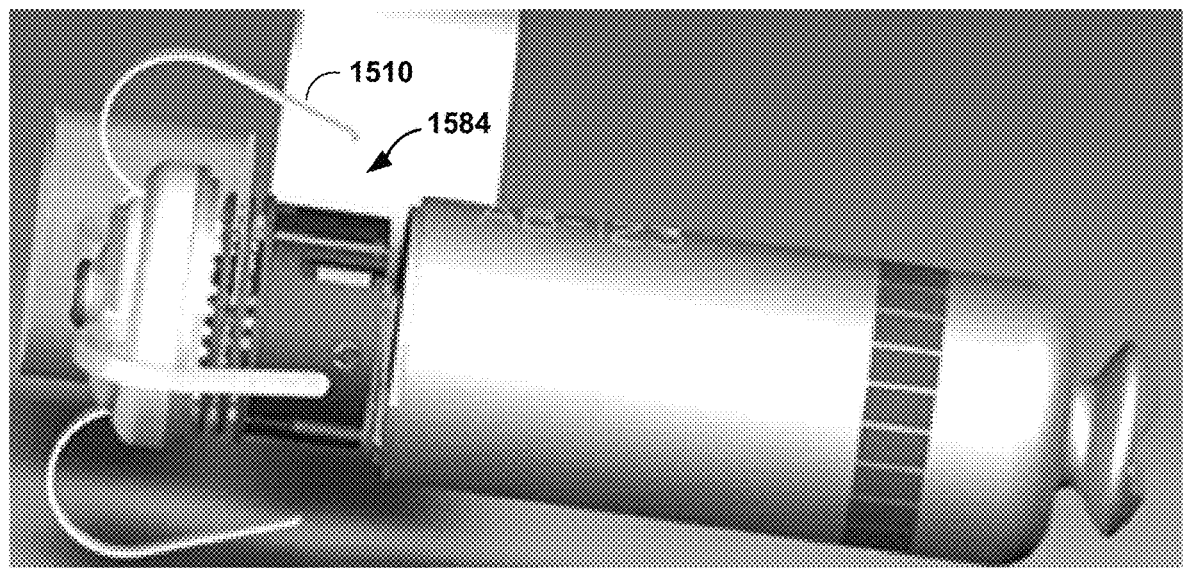
FIGS. 15-17 are exploded view diagrams of an example implantable medical device, in accordance with one or more aspects of this disclosure.
Figure 16:
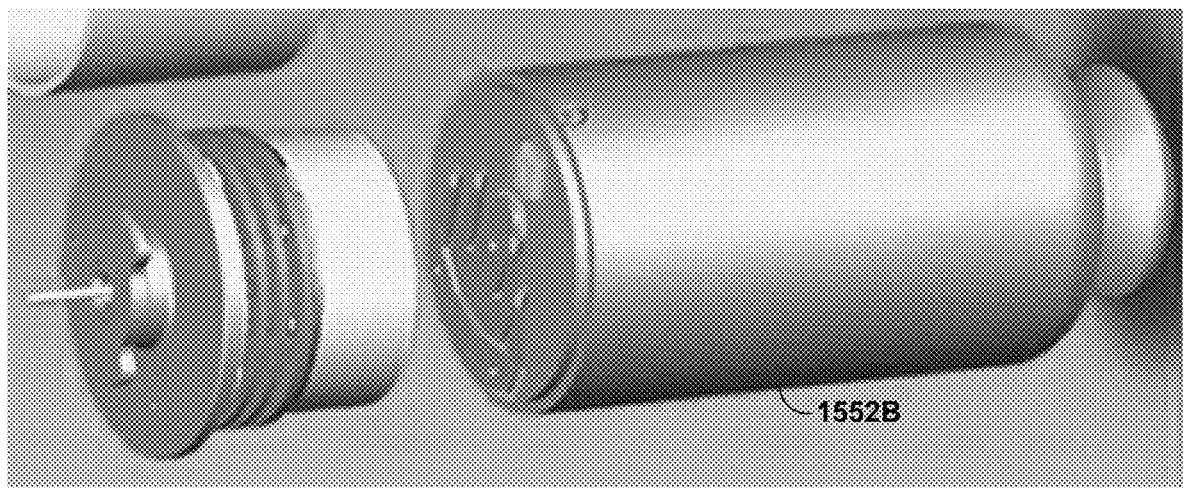
Figure 17:
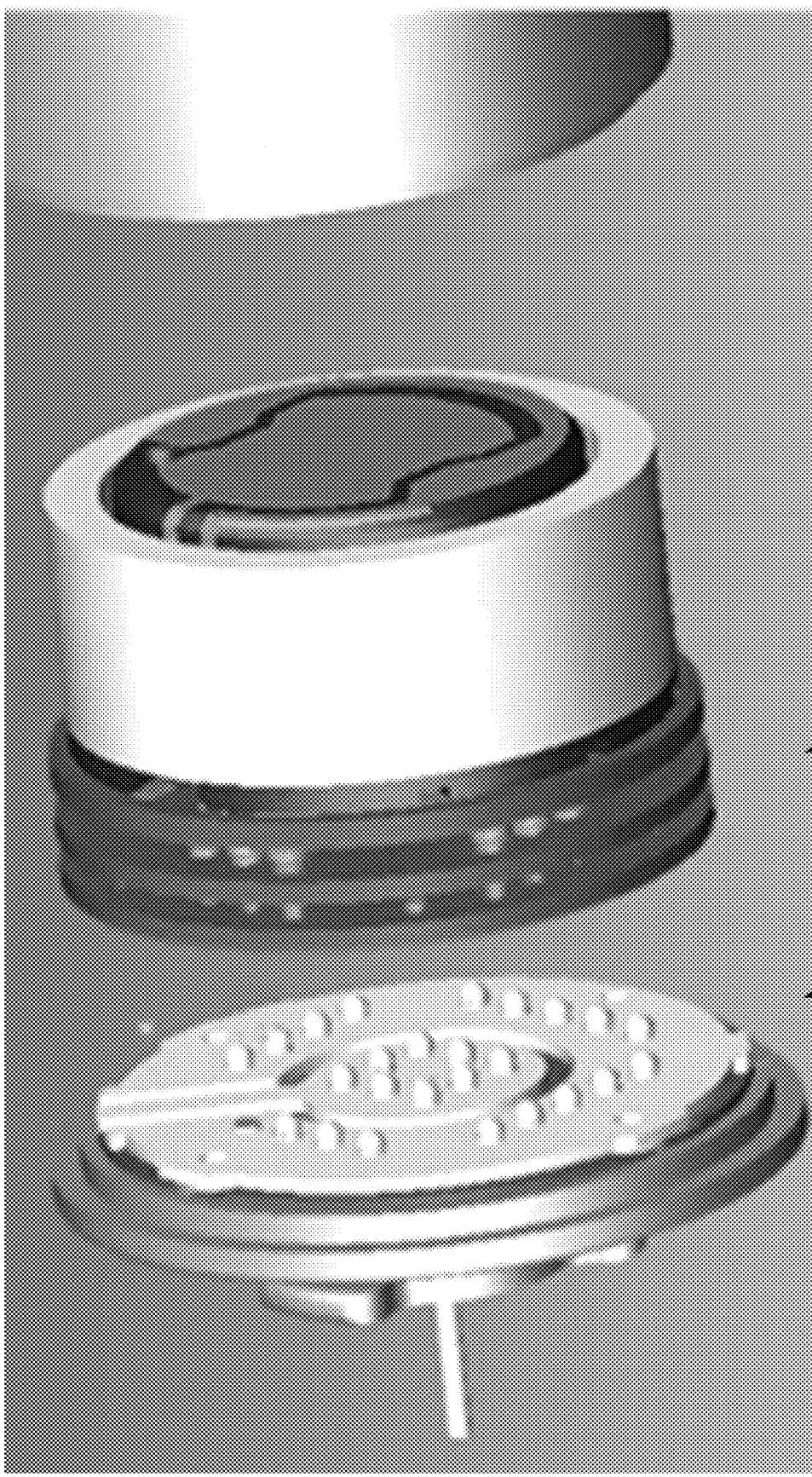

FIGS. 15-17 are exploded view diagrams of an example implantable medical device 1500, in accordance with one or more aspects of this disclosure. As shown in FIGS. 15-17, the circuit layers of electronics module 1584 are oriented perpendicular to the longitudinal axis of implantable medical device 1500 (e.g., the x-axis direction), where the longitudinal axis extends between the ends of implantable medical device 1500. Whereas circuit board 1290 shown in FIG. 12 is parallel with the x-y plane, the circuit layers of electronics module 1584 are parallel with the y-z plane. Thus, electronics module 1584 shown in FIGS. 15-17 has a different orientation than electronics module 1284 shown in FIG. 12. In the example shown in FIGS. 15-17, electronics module 1584 includes three circuit layers, where each layer may include a circuit board and/or another structure include electronics components. Each layer may include a silicon chip overmolded in epoxy, where the chip is embedded in the epoxy. Thus, each circuit layer of electronics module 1584 defines a plane that intersects the longitudinal axis at a single point because the plane of each circuit layer is normal to the longitudinal axis. FIGS. 15-17 depicts each circuit layer of electronics module 1584 as arranged parallel to the other circuit layers.

Electric contact assembly 1586B can be attached to end cap 1572 before installing electronics module 1584. A second side of electronics module 1584 is attached to electric contact assembly 1586B and end cap 1572 by soldering or other attachment means (e.g., conductive epoxy). Electronics module 1584 is then installed by pressing a first side of electronics module 1584 against electric contact assembly 1586A. A housing portion (not shown in FIGS. 15-17) can be installed over electronics module 1584, and end cap 1572. The spring contacts of electric contact assembly 1586A and housing portion 1552B are welded to the header of end cap 1572 and the flange of the battery inside housing portion 1552B.

As shown in FIG. 17, electric contact assembly 1586B may not include any spring contact fingers. Instead, electric contact assembly 1586B can include solder bumps arranged on two conductive portions of electric contact assembly 1586B. The solder bumps of electric contact assembly 1586B may be pre-formed solder bumps that are reflowed to permanently connect a layer of electronics module 1584. The orientation of the layers of electronics module 1584 can make the connection process electric contact assembly 1586B easier than for a perpendicular circuit board as shown in FIGS. 10-14. Electric contact assembly 1586B may include redundant solder points for contacting electronics module 1584. The solder points may be attached to a titanium plate using a sputter process by sputtering the titanium with nickel vanadium to make the titanium solderable. However, in some examples, both of electric contact assemblies 1586A and 1586B may include spring contacts, as shown for electric contact assembly 1586A in FIG. 16.

Each conductive portion of electric contact assembly 1586B may be electrically connected to a pole of the battery. In a single-channel configuration, all of the conductive portions of electric contact assembly 1586B may be connected to the same pole of a battery. In a multiple-channel configuration, a first conductive portion of electric contact assembly 1586B may be connected to a first pole of a battery, and a second conductive portion of electric contact assembly 1586B may be connected to a second pole of the battery. Electric contact assembly 1586B may be spring finger flattened and soldered, thermal compression bonded, and/or epoxy bonded. Electronics module 1584 is rotated ninety degrees with respect to the electronics modules of FIGS. 10-14, which makes soldering the board of electronics module 1584 to electric contact assembly 1586B more practical. Electronics module 1584 and electric contact assembly 1586B may be combined as a layered assembly for use as a build platform in the assembly process. The build platform may be inserted as a single piece into housing portion 1552B. Thus, there may be not be a housing portion between end cap 1572 and housing portion 1552B.

FIG. 18A is a diagram of an example implantable medical device 1800 including an electric contact assembly 1886A with two spring fingers 1830 and 1832, in accordance with one or more aspects of this disclosure. Implantable medical device 1800 includes a single-channel battery connection for electric contact assembly 1886A, where spring finger 1830 is electrically connected to spring finger 1832. Spring fingers 1830 and 1832 may be electrically connected to a first pole of the battery, housing portion 1852A may be electrically connected to a second pole of the battery, and spring fingers 1830 and 1832 may be electrically isolated from housing portion 1852A. FIG. 18A does not show the internal battery connections or a second housing portion that may be connected to housing portion 1852B. In addition, spring fingers 1830 and 1832 may be electrically connected to an electrode on the exterior of IMD 1800.

Figure 18A:
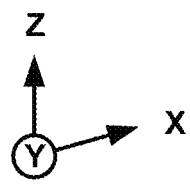

In the example shown in FIG. 18A, electric contact assembly 1886A is mounted on side wall 1834. Side wall 1834 can electrically insulate electric contact assembly 1886A from housing portion 1852A. Electric contact assembly 1886A can electrically connect an electronics module to a first pole of the battery, and housing portion 1852A may electrically connect the electronics module to a second pole of the battery through a second electric contact assembly and a second housing portion (not shown in FIG. 18).

Housing portion 1852A can be welded to a second housing portion that is not shown in FIG. 18A to complete the connection of the second battery pole. Electric contact assembly 1886A may allow for forming a weld at a different position on housing portion 1852A, as compared a weld formed between housing portions 1452A and 1452B, as shown in FIG. 14. For example, a weld may be formed on side wall 1836 between housing portion 1852B and another housing portion that is not shown in FIG. 18A.

In the example shown in FIG. 18A, spring fingers 1830 and 1832 (e.g., spring beams and/or spring arms) are arranged in a mirrored configuration where spring finger 1830 extends from side wall 1834 in the positive z-axis direction, and spring finger 1832 extends from side wall 1834 in the negative z-axis direction. When an electronics module is pressed against electric contact assembly 1886A, spring finger 1830 may provide a force in the negative x-axis direction and in the negative z-axis direction, and spring finger 1832 may provide a force in the negative x-axis direction and in the positive z-axis direction. The mirrored configuration of spring fingers 1830 and 1832 can provide structural stability when an electronics module is connected to spring fingers 1830 and 1832. In some examples, spring fingers 1830 and 1832 may have a shape that is similar to spring contacts 430, 432, 434, and 436 shown in FIGS. 4-6, a shape that is similar to spring contacts 730, 732, 734, and 736 shown in FIGS. 7 and 8, and/or a shape that is similar to the spring contacts shown in FIGS. 9A and 9B.

Figure 18B:
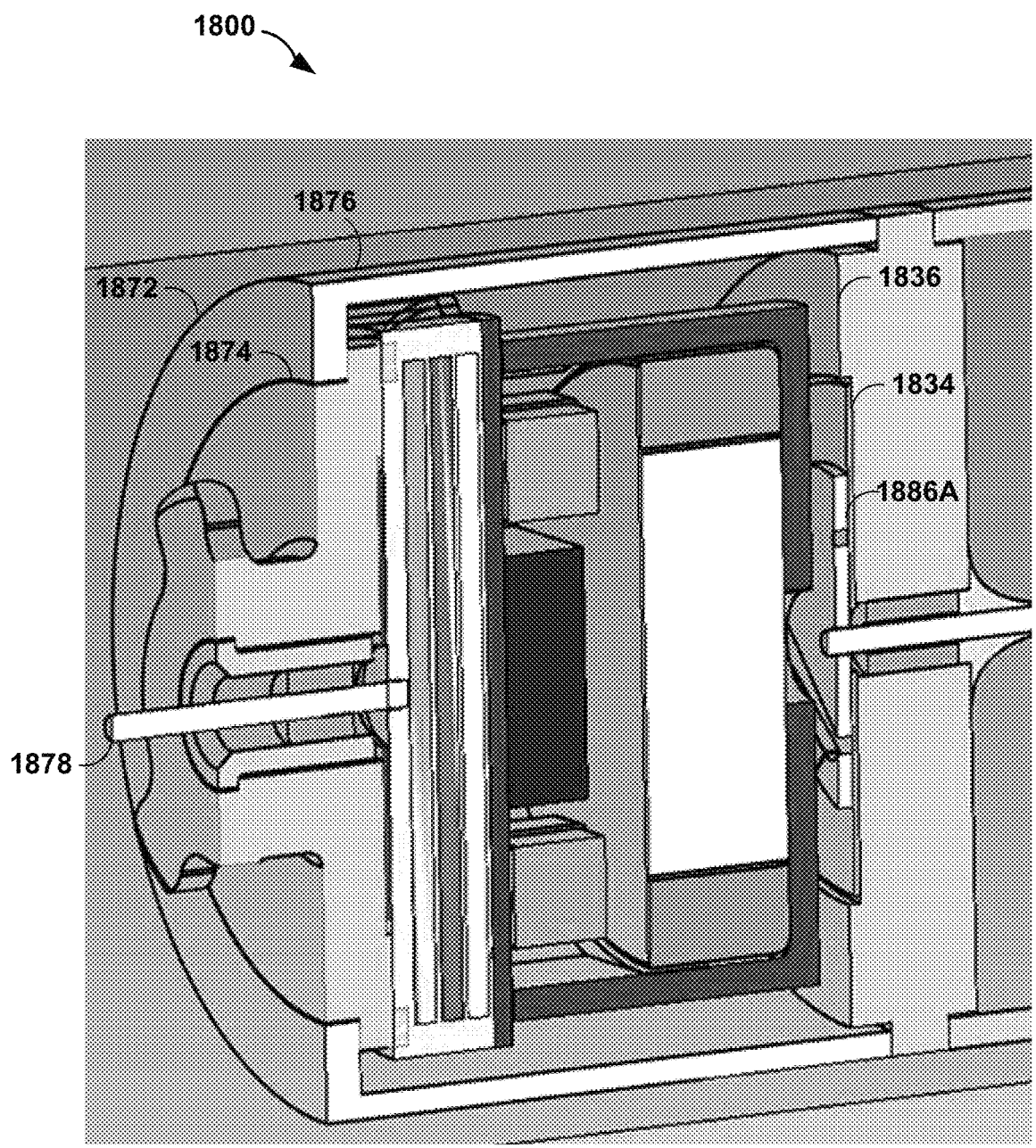
FIG. 18B is a cut-away diagram of an example implantable medical device including an end cap and a feedthrough header, in accordance with one or more aspects of this disclosure.

As shown in FIG. 18A, electric contact assembly 1886A includes a weld tab in the feedthrough pin interface, whereas electric contact assembly 1886A shown in FIG. 18B includes a plate and a pin extending through the plate. Thus, the weld configuration for electric contact assembly 1886A shown in FIG. 18A is different from the weld configuration for electric contact assembly 1886A shown in FIG. 18B.

FIG. 18B is a cut-away diagram of an example implantable medical device 1800 including an end cap 1872 and a feedthrough header 1874, in accordance with one or more aspects of this disclosure. Feedthrough header 1874 provides an electrical channel for electrode 1878 to pass through the exterior of implantable medical device 1800. When implantable medical device 1800 is implanted in the body of a patient, electrode 1878 may be in contact with the tissue of the patient.

During the construction of implantable medical device 1800, a weld may be formed at the interface of end cap 1872 and feedthrough header 1874. Another implantable medical device, such as implantable medical devices 1400 and 1300 shown in FIGS. 13 and 14, may include a weld on the outside diameter of a housing portion. Location 1876 shown in FIG. 18B is one example of a position for a weld on the outside diameter of a housing portion.

Figure 19:
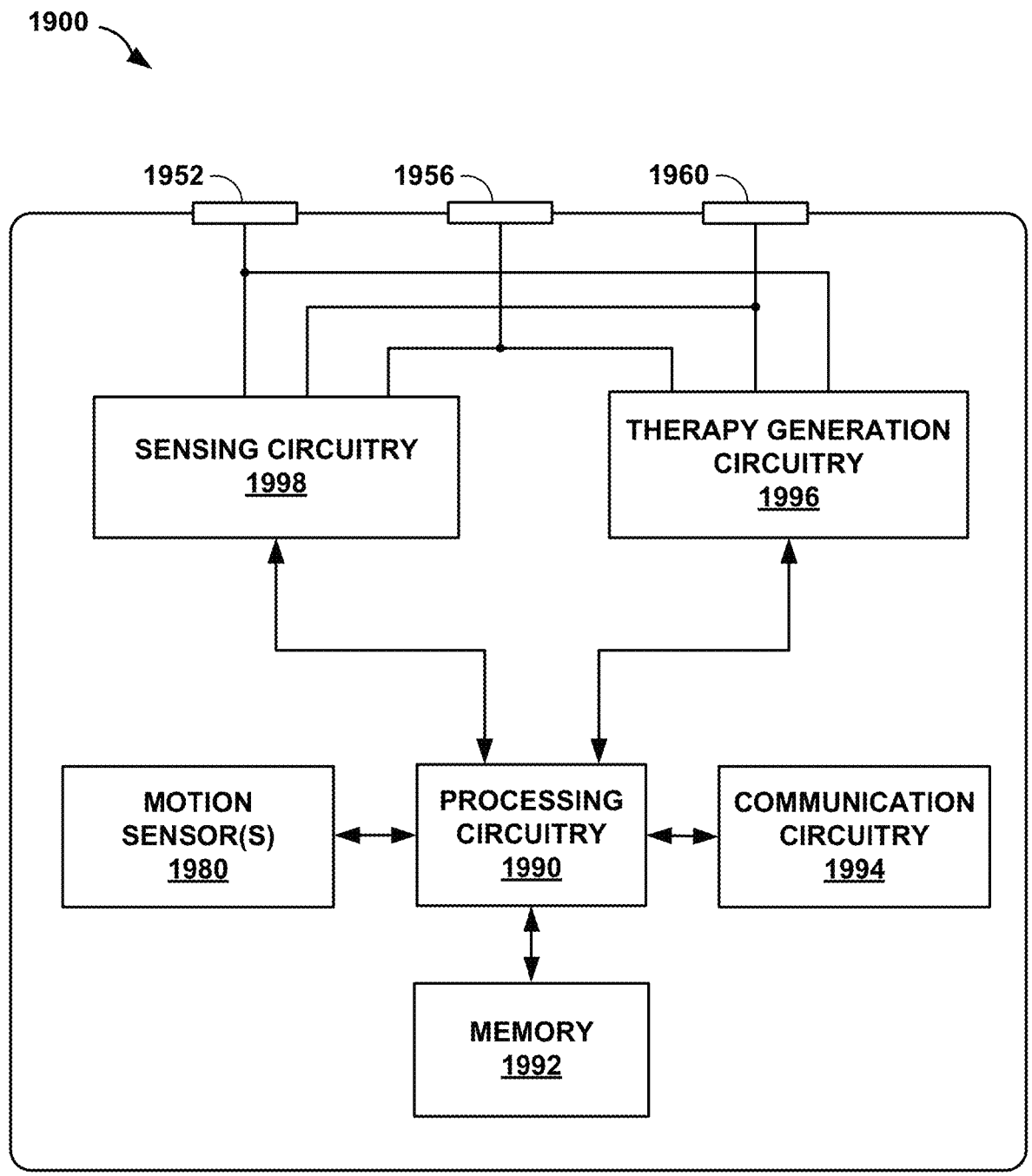
FIG. 19 is a conceptual block diagram of an example implantable medical device, in accordance with one or more aspects of this disclosure.

FIG. 19 is a conceptual block diagram of an example implantable medical device 1900, in accordance with one or more aspects of this disclosure. In the illustrated example, implantable medical device 1900 includes processing circuitry 1990, memory 1992, therapy generation circuitry 1996, sensing circuitry 1998, motion sensor 1980, and communication circuitry 1994. One or more of the elements of implantable medical device 1900 may be part of an electronics module. For example, processing circuitry 1990, memory 1992, therapy generation circuitry 1996, sensing circuitry 1998, motion sensor 1980, and/or communication circuitry 1994 may be mounted on a circuit board of an electronics module of implantable medical device 1900.

Memory 1992 includes computer-readable instructions that, when executed by processing circuitry 1990, cause implantable medical device 1900 and processing circuitry 1990 to perform various functions of implantable medical device 1900 such as storing and analyzing signals received by implantable medical device 1900 and providing pacing therapy for a patient's heart. Example details of functions of implantable medical device 1900 can be found in commonly assigned U.S. Patent Application Publication No. 2019/0209845 entitled "Adaptive Cardiac Resynchronization Therapy," filed on Mar. 22, 2018, the entire contents of which are incorporated herein by reference.

Memory 1992 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media.

Processing circuitry 1990 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 1990 may include multiple components, such as any combination of one or more microprocessors, one or more controllers, one or more DSPs, one or more ASICs, or one or more FPGAs, as well as other discrete or integrated logic circuitry. The functions attributed to processing circuitry 1990 herein may be embodied as software, firmware, hardware or any combination thereof.

Processing circuitry 1990 controls therapy generation circuitry 1996 to deliver stimulation therapy to a patient's heart according to therapy parameters, which may be stored in memory 1992. For example, processing circuitry 1990 may control therapy generation circuitry 1996 to deliver electrical pulses with the amplitudes, pulse widths, frequency, or electrode polarities specified by the therapy parameters. In this manner, therapy generation circuitry 1996 may deliver pacing pulses to the heart via electrodes 1952, 1956, and/or 1960. Although implantable medical device 1900 may only include two electrodes, e.g., electrodes 1952 and 1960, implantable medical device 1900 may utilize three or more electrodes in other examples. Implantable medical device 1900 may use any combination of electrodes to deliver therapy and/or detect electrical signals from the patient.

Therapy generation circuitry 1996 is electrically coupled to electrodes 1952, 1956, and/or 1960 positioned on the housing of implantable medical device 1900. In the illustrated example, therapy generation circuitry 1996 is configured to generate and deliver electrical stimulation therapy to the heart. For example, therapy generation circuitry 1996 may deliver pulses to a portion of cardiac muscle within the heart via electrodes 1952, 1956, and/or 1960. In some examples, therapy generation circuitry 1996 may deliver pacing stimulation in the form of electrical pulses. Therapy generation circuitry 1996 may include charging circuitry, and one or more charge storage devices, such as one or more capacitors. Switching circuitry (not shown) may control when the capacitor(s) are discharged to electrodes 1952 and 1960.

Sensing circuitry 1998 monitors signals from at least one of electrodes 1952, 1956, and 1960 to monitor electrical activity of the heart, impedance, or another electrical phenomenon. Sensing may be done to determine heart rates or heart rate variability, or to detect ventricular dyssynchrony, arrhythmias (e.g., tachyarrhythmias) or other electrical signals. Sensing circuitry 1998 may include switching circuitry to select the electrode polarity used to sense the heart activity. In examples with more than two electrodes, processing circuitry 1990 may select the electrodes that function as sense electrodes, i.e., select the sensing configuration, via the switching circuitry within sensing circuitry 1998. In some examples, electrode 1952 is connected to a first pole of a battery of implantable medical device 1900 (e.g., the positive terminal of the battery), electrode 1960 is connected to a second pole of the battery (e.g., the case ground), and electrode 1956 is a sense electrode configured to receive signals in the environment surrounding implantable medical device 1900. Other configurations of electrodes 1952, 1956, and 1960 are also possible.

Motion sensor 1980 may be contained within the housing of implantable medical device 1900 and include one or more accelerometers, gyroscopes, electrical or magnetic field sensors, or other devices capable of detecting motion and/or position of implantable medical device 1900. For example, motion sensor 1980 may include a three-axis accelerometer (three-dimensional accelerometer) that is configured to detect accelerations in any direction in space. Specifically, the three-axis accelerometer may be used to detect the motion of implantable medical device 1900 that may be indicative of cardiac events and/or noise.

When processing circuitry 1990 controls therapy generation circuitry 1996 to deliver ventricular pacing pulses for CRT, processing circuitry 1990 may also control motion sensor(s) 1980 to generate a signal that varies with the cardiac contraction. In some examples, motion sensor(s) 1980 may generate the signal substantially continuously. For each cardiac cycle during which a ventricular pacing pulses is delivered, processing circuitry 1990 may identify one or more features of the cardiac contraction within the signal.

Processing circuitry 1990 may determine whether the contraction is a fusion beat or other type of beat, e.g., intrinsic or fully-paced, based on the one or more features.

Communication circuitry 1994 includes any suitable hardware, firmware, software or any combination thereof for communicating with another device, such as an external device or another implantable device. In some examples, communication circuitry 1994 may be configured for tissue conductive communication with another implantable medical device via electrodes 1952, 1956, and/or 1960. Implantable medical device 1900 may communicate with an external device via the other implantable medical device, or communication circuitry 1994 may be configured for radio-frequency communication with an external device, e.g., via an antenna.

Figure 20:
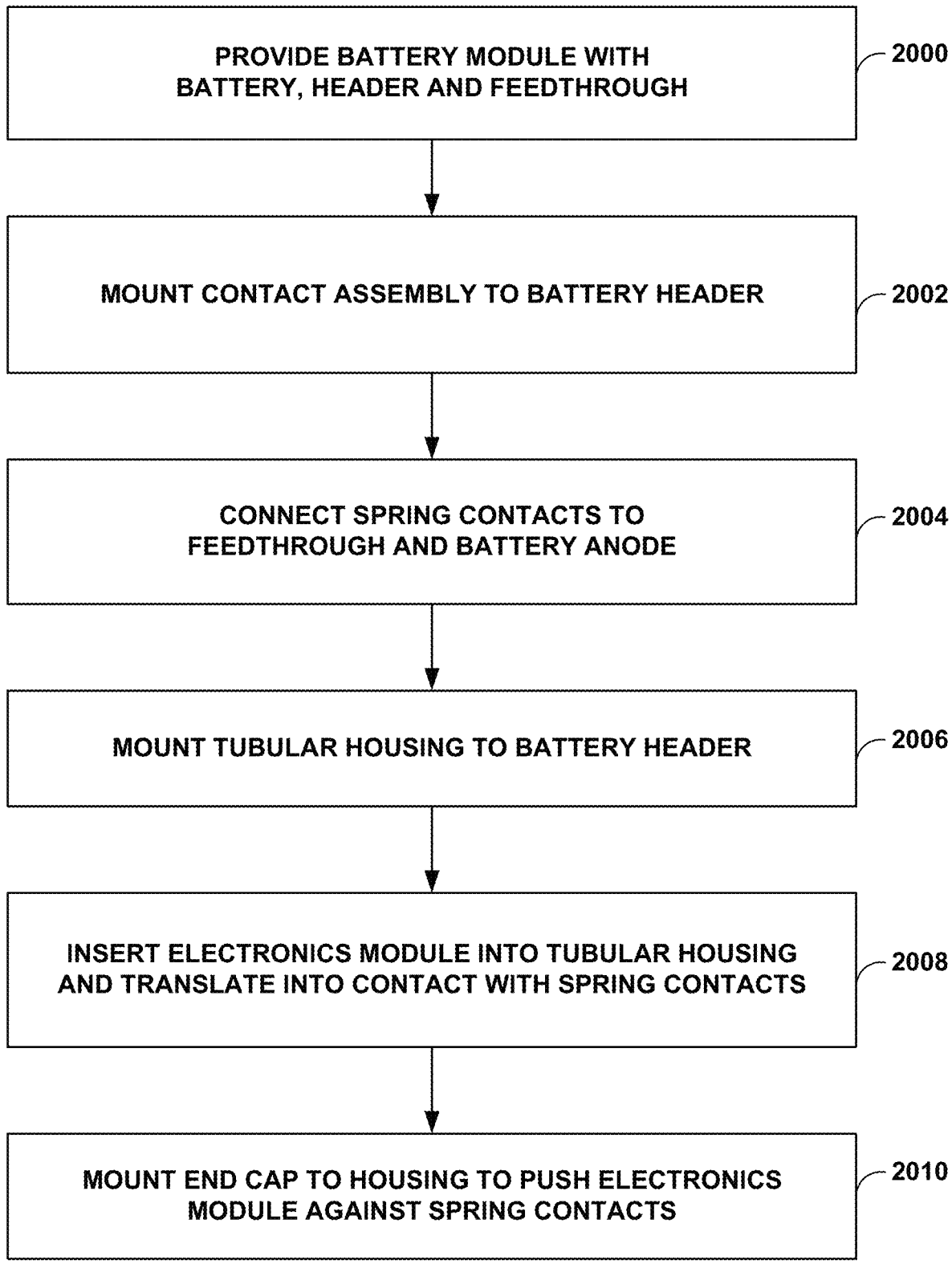
FIG. 20 is a flow diagram illustrating an example process for assembling an implantable medical device, in accordance with one or more aspects of this disclosure.

FIG. 20 is a flow diagram illustrating an example process for assembling an implantable medical device, in accordance with one or more aspects of this disclosure. The techniques of FIG. 20 are described with reference to implantable medical device 1400 shown in FIG. 14, although other components may exemplify similar techniques.

In the example of FIG. 20, a battery module including a battery, a battery header, and a feedthrough are provided within housing portion 1452B (2000). The battery header is attached to the battery, where the battery header is positioned in the positive x-axis direction from the battery. The feedthrough includes a conductive material extending through battery header to provide an electrical connection through battery header. Side wall 1470 may be part of the battery header, or side wall 1470 may be separate from and attached to electric contact assembly 1486A.

In the example of FIG. 20, electric contact assembly 1486A is mounted to the battery header (2002). Additionally or alternatively, electric contact assembly 1486A may be mounted to side wall 1470. Electric contact assembly 1486A may be soldered, welded, or adhered to the battery header. The spring contacts of electric contact assembly 1486A are connected to the battery anode and the feedthrough of the battery header (2004). In examples in which electric contact assembly 1486A includes more than one spring contact, a first spring contact may be connected to the anode of the battery and a second spring contact may be connected to the cathode of the battery, which is referred to as a multiple-channel configuration. In a single-channel configuration, the first and second spring contacts may both be connected to the same pole of the battery.

In the example of FIG. 20, housing portion 1452A is mounted to the battery header (2006). Housing portion 1452A can be mounted to the battery header and/or side wall 1470. Electronics module 1484 is then inserted into housing portion 1452A and comes into contact with the spring contacts of electric contact assembly 1486A (2008). Electric contact assembly 1486A forms the floor of the chamber, and electronics module 1484 is dropped into the chamber. In some examples, zero, one, or both of electric contact assemblies 1486A and 1486B may be permanently attached to electronics module 1484 using solder, adhesive, and/or conductive epoxy. In examples in which neither of electric contact assemblies 1486A and 1486B is permanently attached to electronics module 1484, electronics module 1484 can be held in place by the pressure applied by the spring contacts of electric contact assemblies 1486A and 1486B.

End cap 1472 is mounted to housing portion 1452A to push electronics module 1484 against the spring contacts of electric contact assemblies 1486A and 1486B (2010). Before mounting end cap 1472 on housing portion 1452A, electric contact assembly 1486B can be attached to end cap 1472, so that the combined structure of end cap 1472 and electric contact assembly 1486B is mounted to housing portion 1452A. The spring contacts of electric contact assembly 1486B may be electrically connected to an electrode of end cap 1472 by a feedthrough (e.g., a conductive path through the hermetic seal of implantable medical device 1400). When end cap 1472 is mounted, end cap 1472 covers the top end of the chamber. The enclosure of implantable medical device 1400 may be laser welded by laser welding end cap 1472 to housing portion 1452A. Implantable medical device 1400 may also include end cap 1458 that is laser welded to housing portion 1452B or electrode 1460. Electric contact assembly 1486B may be pre-connected to end cap 1472 such that there is an electrical connection between a spring contact of electric contact assembly 1486B and a sense electrode on end cap 1472 via a feedthrough pin. After assembly, housing portion 1452A can be welded to the headers to seal the enclosure around electronics module 1484.

Before end cap 1472 is mounted to housing portion 1452A, electric contact assembly 1486B can be attached to end cap 1472. Then the combined structure of end cap 1472 and electric contact assembly 1486B can be pressed against and/or permanently attached to electronics module 1484.

Figure 21:
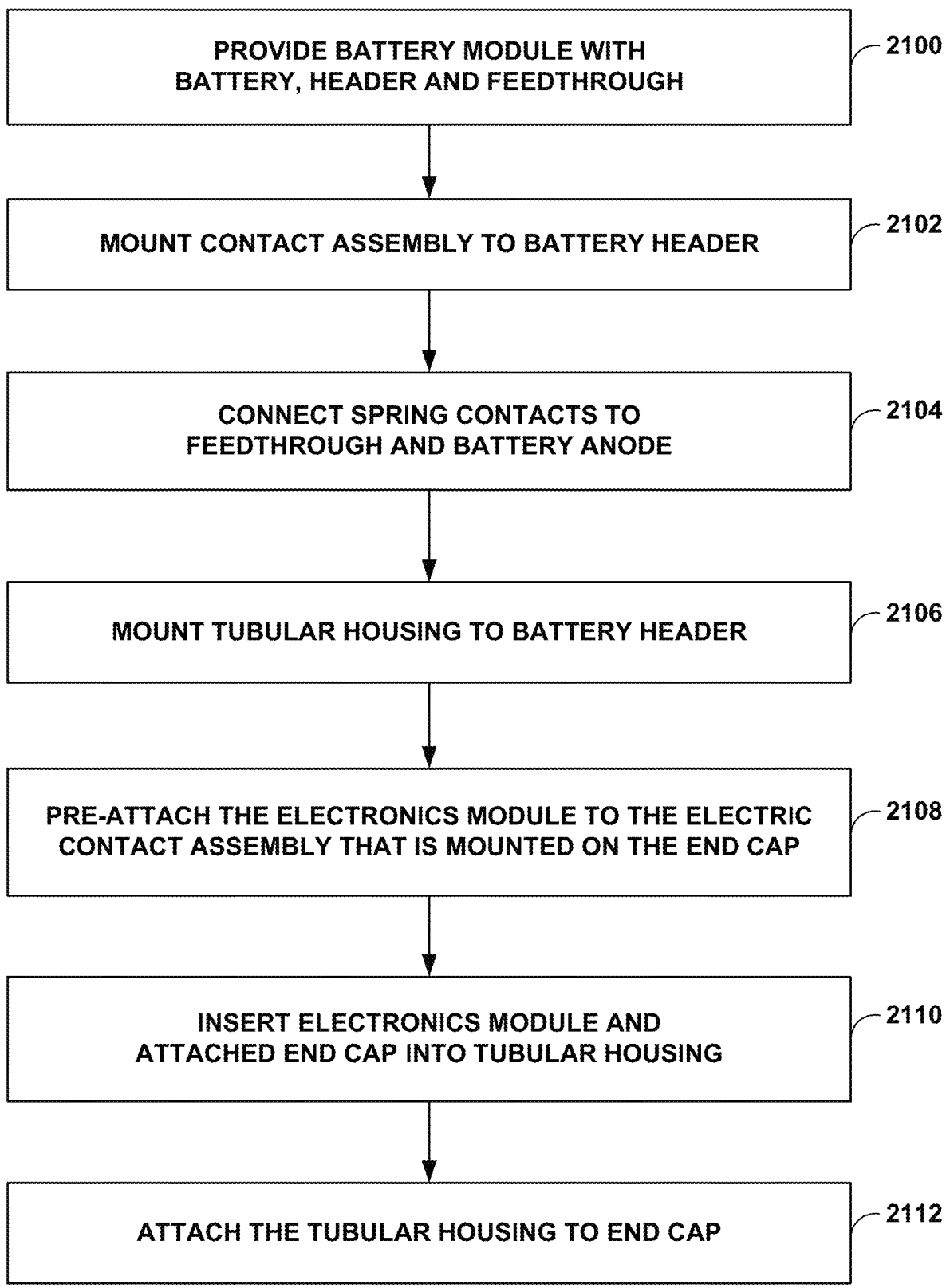
FIG. 21 is a flow diagram illustrating an example process for assembling an implantable medical device with a permanent attachment on at least one electric contact assembly, in accordance with one or more aspects of this disclosure.

FIG. 21 is a flow diagram illustrating an example process for assembling an implantable medical device with a permanent attachment on at least one electric contact assembly, in accordance with one or more aspects of this disclosure. The techniques of FIG. 21 are described with reference to implantable medical device 1400 shown in FIG. 14, although other components may exemplify similar techniques. The techniques described with respect to the flow diagram of FIG. 21 can be implemented with only one electric contact assembly having spring contacts. For example, one end of electronics module 1484 may be pressed against an electric contact assembly having spring contacts, where the other end of electronics module 1484 is soldered to an electric contact assembly having solder bumps.

Steps 2100, 2102, 2104, and 2106 shown in FIG. 21 are similar to steps 2000, 2002, 2004, and 2006 shown in FIG. 20. In the example of FIG. 21, a battery module including a battery, a battery header, and a feedthrough are provided within housing portion 1452B (2100). Electric contact assembly 1486A is mounted to the battery header (2102). The spring contacts of electric contact assembly 1486A can be connected to the battery anode and the feedthrough of the battery header (2104). Housing portion 1452A is mounted to the battery header (2106).

Electronics module 1484 is pre-attached to electric contact assembly 1486B, which is mounted on end cap 1472 (2108). Electronics module 1484 can be connected to electric contact assembly 1486B using a solder process. Electric contact assembly 1486B may include solder bumps similar to electric contact assembly 1586B shown in FIG. 17. The solder bumps of electric contact assembly 1486B can be reflowed to form a permanent connection with electronics module 1484. The combined structure of electronics module 1484, electric contact assembly 1486B, and end cap 1472 can be a pre-assembled structure that is shipped to the final manufacturing location where steps 2110 and 2112 are performed.

The combined structure of electronics module 1484 and end cap 1472 is then inserted into housing portion 1452A (2110). Housing portion 1452A can be attached to end cap 1472 by welding or using another attachment process (2112).

Various examples of the disclosure have been described. Any combination of the described systems, operations, or functions is contemplated. These and other examples are within the scope of the following claims.

What is claimed is:

1. An implantable medical device comprising:
   a battery;
   an electronics module electrically connected to the battery;
   an elongated housing comprising a side wall positioned between the battery and an end cap, wherein the electronics module is positioned within the elongated housing between the battery and the end cap; and
   an electrical contact assembly comprising a first spring contact and a second spring contact,
   wherein the electrical contact assembly is positioned within the elongated housing between the electronics module and the battery or is positioned within the elongated housing between the electronics module and the end cap.

2. The device of claim 1, further comprising a battery header and an electrical feedthrough electrically connected to the battery and extending through the battery header, wherein the electrical contact assembly is positioned between the electronics module and the battery header and electrically connected to the electrical feedthrough and the electronics module.

3. The device of claim 2, wherein the electrical contact assembly is a first electrical contact assembly, wherein the electrical feedthrough is a first electrical feedthrough, and further comprising:
   a second electrical feedthrough extending through the end cap, and
   a second electrical contact assembly comprising a third spring contact and a fourth spring contact,
   wherein the second electrical contact assembly is positioned within the housing between the electronics module and the end cap and electrically connected to the second electrical feedthrough and the electronics module, and
   wherein at least one of the first, second, third, or fourth spring contacts is permanently attached to the electronics module.

4. The device of claim 1, wherein the electrical contact assembly further comprises an insulative backing, wherein the first and second spring contacts are mounted to the insulative backing, and wherein each of the first and second spring contacts comprises a contact arm biased away from the insulative backing.

5. The device of claim 4, wherein each of the first and second spring contacts comprise a plurality of contact arms biased away from the insulative backing.

6. The device of claim 4, wherein the contact arm comprises an electrically conductive plating.

7. The device of claim 4, wherein an end of the contact arm comprises a raised contact surface.

8. The device of claim 1, further comprising an electrical feedthrough extending through the end cap, wherein the electrical contact assembly is positioned between the electronics module and the end cap and electrically connected to the electrical feedthrough and the electronics module.

9. The device of claim 1,
   wherein the electrical contact assembly further comprises a third spring contact and a fourth spring contact, and wherein the first, second, third, and fourth spring contacts are pressed against the electronics module.

10. The device of claim 1, further comprising an electrode positioned on an exterior of the device and electrically isolated from the elongated housing,
   wherein the first spring contact is electrically connected to the elongated housing,
   wherein the second spring contact is electrically connected to the electrode, and
   wherein the first spring contact is electrically isolated from the second spring contact.

11. The device of claim 1, further comprising an electrode positioned on an exterior of the device and electrically isolated from the elongated housing,
   wherein the first spring contact is electrically connected to the second spring contact,
   wherein the first spring contact is electrically connected to the electrode, and
   wherein the first spring contact and the second spring contact are electrically isolated from the elongated housing.

12. The device of claim 1, wherein the electronics module comprises one or more circuit layers oriented perpendicular to a longitudinal axis of the elongated housing.

13. The device of claim 1, wherein the electronics module comprises a plurality of circuit layers located adjacent to each other and oriented perpendicular to a longitudinal axis of the elongated housing.

14. The device of claim 1, wherein the electronics module comprises a circuit board oriented parallel to or along a longitudinal axis of the elongated housing.

15. The device of claim 1, wherein when assembled, at least one of the first spring contact or the second spring contact applies pressure in a direction parallel to a longitudinal axis of the housing and toward the electronics module.

* * * * *